(12) United States Patent
Smith et al.

(10) Patent No.: US 8,807,997 B2
(45) Date of Patent: *Aug. 19, 2014

(54) REDUCED-FRICTION BUCCAL TUBE AND METHOD OF USE

(71) Applicant: RMO, Inc., Denver, CO (US)

(72) Inventors: Jeffrey Smith, Denver, CO (US); Leon W. Laub, Fort Collins, CO (US)

(73) Assignee: RMO, Inc., Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/049,730

(22) Filed: Oct. 9, 2013

(65) Prior Publication Data

US 2014/0038121 A1  Feb. 6, 2014

Related U.S. Application Data

(63) Continuation of application No. 13/595,548, filed on Aug. 27, 2012, now Pat. No. 8,585,399, which is a continuation of application No. 11/852,057, filed on Sep. 7, 2007, now Pat. No. 8,251,697.

(60) Provisional application No. 60/824,891, filed on Sep. 7, 2006.

(51) Int. Cl.
*A61C 3/00* (2006.01)
(52) U.S. Cl.
USPC .............................................. 433/17; 433/10
(58) Field of Classification Search
USPC .......................................................... 433/8–17
See application file for complete search history.

(56) References Cited

U.S. PATENT DOCUMENTS

| | | | |
|---|---|---|---|
| 626,476 | A | 6/1899 | Angle |
| 1,890,487 | A | 12/1932 | Angle |
| 2,011,575 | A | 8/1935 | Ford |
| 2,104,192 | A | 1/1938 | Ford |
| 2,196,515 | A | 4/1940 | Atkinson |
| 3,028,671 | A | 4/1962 | Berger |
| 3,055,110 | A | 9/1962 | Kesling |
| 3,158,934 | A | 12/1964 | Waldman |
| 3,193,930 | A | 7/1965 | Bien |
| 3,391,461 | A | 7/1968 | Johnson |
| 3,435,527 | A | 4/1969 | Kesling |
| 3,494,034 | A | 2/1970 | Kesling |
| 3,504,438 | A | 4/1970 | Wittman et al. |
| 3,526,961 | A | 9/1970 | Kesling |

(Continued)

FOREIGN PATENT DOCUMENTS

| | | |
|---|---|---|
| DE | 8903611 | 8/1990 |
| DE | 69228472 | 10/1999 |

(Continued)

OTHER PUBLICATIONS

U.S. Appl. No. 10/821,699, filed Apr. 9, 2004, Ricketts.

(Continued)

*Primary Examiner* — Eric Rosen
(74) *Attorney, Agent, or Firm* — Sheridan Ross P.C.

(57) ABSTRACT

An orthodontic appliance includes features for reducing friction between an interior of an archwire slot portion of the appliance and an archwire to be placed within the archwire slot. Other embodiments include a rounded exterior occlusal surface. Embodiments further include one or more receptacles for receiving an installation tool.

20 Claims, 18 Drawing Sheets

(56) References Cited

U.S. PATENT DOCUMENTS

| | | |
|---|---|---|
| 3,765,091 A | 10/1973 | Northcutt |
| 3,798,773 A | 3/1974 | Northcutt |
| 3,838,514 A | 10/1974 | Polak |
| 3,854,207 A | 12/1974 | Wildman |
| 3,874,080 A | 4/1975 | Wallshein |
| 3,916,526 A | 11/1975 | Schudy |
| 3,964,156 A | 6/1976 | Williams et al. |
| 3,975,824 A | 8/1976 | Lee |
| 3,985,282 A | 10/1976 | Miller et al. |
| 3,987,547 A | 10/1976 | Moss |
| 4,015,334 A | 4/1977 | Moss |
| 4,028,809 A | 6/1977 | Wallshein |
| 4,083,113 A | 4/1978 | Miller et al. |
| 4,103,423 A | 8/1978 | Kessel |
| 4,134,208 A | 1/1979 | Pearlman |
| 4,171,568 A | 10/1979 | Forster |
| 4,172,999 A | 10/1979 | Leidich |
| 4,183,141 A | 1/1980 | Dellinger et al. |
| 4,192,070 A | 3/1980 | Lemchen et al. |
| 4,193,195 A | 3/1980 | Merkel et al. |
| 4,197,642 A | 4/1980 | Wallshein |
| 4,212,638 A | 7/1980 | Korn |
| 4,219,617 A | 8/1980 | Wallshein |
| D256,950 S | 9/1980 | Sable |
| 4,242,085 A | 12/1980 | Wallshein |
| 4,248,587 A | 2/1981 | Kurz |
| 4,260,375 A | 4/1981 | Wallshein |
| 4,284,405 A | 8/1981 | Dellinger |
| 4,299,569 A | 11/1981 | Frantz |
| 4,302,532 A | 11/1981 | Wallshein |
| 4,322,206 A | 3/1982 | Reynolds |
| 4,350,487 A | 9/1982 | Kesling et al. |
| 4,354,834 A | 10/1982 | Wilson |
| 4,386,908 A | 6/1983 | Kurz |
| 4,415,330 A | 11/1983 | Daisley et al. |
| 4,419,078 A | 12/1983 | Pletcher |
| 4,430,061 A | 2/1984 | Webb et al. |
| 4,455,137 A | 6/1984 | Diamond |
| 4,462,800 A | 7/1984 | Jones |
| 4,478,577 A | 10/1984 | Warren, Jr. |
| 4,498,867 A | 2/1985 | Kesling |
| 4,511,331 A | 4/1985 | Scebold et al. |
| 4,527,975 A | 7/1985 | Ghafari et al. |
| 4,529,382 A | 7/1985 | Creekmore |
| 4,531,911 A | 7/1985 | Creekmore |
| 4,531,991 A | 7/1985 | Ziemek et al. |
| 4,545,760 A | 10/1985 | Forster |
| 4,551,095 A | 11/1985 | Mason |
| 4,575,337 A | 3/1986 | Fujita |
| 4,626,209 A | 12/1986 | Tsai et al. |
| 4,639,218 A | 1/1987 | Jones et al. |
| 4,659,309 A | 4/1987 | Merkel |
| 4,661,059 A | 4/1987 | Kanno |
| D290,040 S | 5/1987 | Kelly |
| 4,669,979 A | 6/1987 | Snead |
| 4,669,981 A | 6/1987 | Kurz |
| D291,919 S | 9/1987 | Reynolds |
| 4,700,697 A | 10/1987 | Mundell et al. |
| 4,712,999 A | 12/1987 | Rosenberg |
| 4,752,221 A | 6/1988 | Hanson et al. |
| 4,773,853 A | 9/1988 | Kussick |
| 4,781,334 A | 11/1988 | Derichs |
| 4,781,582 A | 11/1988 | Kesling |
| 4,793,804 A | 12/1988 | Schudy |
| 4,795,342 A | 1/1989 | Jones |
| 4,799,882 A | 1/1989 | Kesling |
| 4,819,316 A | 4/1989 | Rossini et al. |
| 4,820,151 A | 4/1989 | Pospisil |
| 4,838,786 A | 6/1989 | Reher et al. |
| 4,854,866 A | 8/1989 | Wilson |
| 4,859,179 A | 8/1989 | Kesling |
| 4,900,251 A | 2/1990 | Andreasen |
| 4,917,602 A | 4/1990 | Broussard |
| 4,927,360 A | 5/1990 | Pospisil |
| 4,927,362 A | 5/1990 | Snead |
| 4,954,080 A | 9/1990 | Kelly et al. |
| 4,963,092 A | 10/1990 | Snead |
| 4,975,052 A | 12/1990 | Spencer et al. |
| 4,997,182 A | 3/1991 | Kussick |
| 5,022,854 A | 6/1991 | Broughton et al. |
| 5,030,089 A | 7/1991 | Kawaguchi |
| 5,035,614 A | 7/1991 | Greenfield |
| 5,044,945 A | 9/1991 | Peterson |
| 5,057,012 A | 10/1991 | Kesling |
| 5,059,119 A | 10/1991 | Snead |
| 5,062,794 A | 11/1991 | Miura |
| 5,066,225 A | 11/1991 | Forbes Jones et al. |
| D322,482 S | 12/1991 | Ianieri et al. |
| 5,095,602 A | 3/1992 | Reher et al. |
| 5,120,218 A | 6/1992 | Hanson |
| 5,125,831 A | 6/1992 | Pospisil |
| 5,125,832 A | 6/1992 | Kesling |
| 5,127,828 A | 7/1992 | Suyama |
| 5,133,740 A | 7/1992 | Kussick |
| 5,151,028 A | 9/1992 | Snead |
| 5,154,607 A | 10/1992 | Hanson |
| 5,158,452 A | 10/1992 | Franseen et al. |
| 5,160,261 A | 11/1992 | Peterson |
| 5,161,969 A | 11/1992 | Pospisil et al. |
| D331,975 S | 12/1992 | Pospisil |
| 5,183,388 A | 2/1993 | Kumar |
| 5,203,804 A | 4/1993 | Nikutowski et al. |
| 5,224,858 A | 7/1993 | Hanson |
| 5,226,814 A | 7/1993 | Allen |
| 5,230,620 A | 7/1993 | Watanabe |
| 5,238,402 A | 8/1993 | Rohlcke et al. |
| 5,242,299 A | 9/1993 | Yoshida |
| D340,523 S | 10/1993 | Barngrover |
| 5,252,066 A | 10/1993 | Fairhurst |
| 5,254,002 A | 10/1993 | Reher et al. |
| 5,267,855 A | 12/1993 | Tuneberg |
| 5,269,680 A | 12/1993 | Kawaguchi |
| 5,277,581 A | 1/1994 | Peterson |
| 5,288,229 A | 2/1994 | Huff et al. |
| 5,292,248 A | 3/1994 | Schultz |
| 5,299,934 A | 4/1994 | Suyama |
| 5,302,117 A | 4/1994 | Kraut et al. |
| 5,302,121 A | 4/1994 | Gagin |
| 5,320,525 A | 6/1994 | Forster |
| 5,320,526 A | 6/1994 | Tuneberg |
| 5,322,435 A | 6/1994 | Pletcher |
| 5,322,613 A | 6/1994 | Ohira |
| 5,356,288 A | 10/1994 | Cohen |
| 5,358,402 A | 10/1994 | Reed et al. |
| 5,362,232 A | 11/1994 | Franseen et al. |
| 5,362,233 A | 11/1994 | Thompson |
| 5,380,196 A | 1/1995 | Kelly et al. |
| 5,383,784 A | 1/1995 | Sernetz |
| 5,395,238 A | 3/1995 | Andreiko et al. |
| D358,649 S | 5/1995 | Moschik |
| D358,650 S | 5/1995 | Moschik |
| D359,776 S | 6/1995 | Hilgers |
| 5,439,379 A | 8/1995 | Hansen |
| 5,441,408 A | 8/1995 | Moschik |
| 5,441,409 A | 8/1995 | Tuneberg |
| 5,443,384 A | 8/1995 | Franseen et al. |
| 5,454,716 A | 10/1995 | Banerjee et al. |
| 5,464,349 A | 11/1995 | Andreiko et al. |
| 5,470,228 A | 11/1995 | Franseen et al. |
| 5,474,444 A | 12/1995 | Wildman |
| 5,474,445 A | 12/1995 | Voudouris |
| 5,505,616 A | 4/1996 | Harwell |
| 5,522,725 A | 6/1996 | Jordan et al. |
| 5,545,037 A | 8/1996 | Takeshi |
| 5,556,277 A | 9/1996 | Yawata et al. |
| 5,562,445 A | 10/1996 | DeVincenzo et al. |
| 5,588,833 A | 12/1996 | Risse |
| 5,595,484 A | 1/1997 | Orikasa et al. |
| 5,597,302 A | 1/1997 | Pospisil et al. |
| 5,607,301 A | 3/1997 | Roman |
| 5,616,026 A | 4/1997 | Cash |
| 5,618,175 A | 4/1997 | Reher et al. |
| 5,620,321 A | 4/1997 | Thornburg et al. |
| 5,622,494 A | 4/1997 | Andreiko et al. |

(56) References Cited

U.S. PATENT DOCUMENTS

| | | |
|---|---|---|
| 5,653,588 A | 8/1997 | Moschik |
| 5,685,711 A | 11/1997 | Hanson |
| 5,692,898 A | 12/1997 | Orikasa et al. |
| 5,707,231 A | 1/1998 | Watt et al. |
| 5,720,611 A | 2/1998 | Teng |
| 5,727,941 A | 3/1998 | Kesling |
| 5,729,768 A | 3/1998 | Fields et al. |
| 5,738,514 A | 4/1998 | DeVincenzo et al. |
| 5,746,592 A | 5/1998 | Nezu et al. |
| 5,746,594 A | 5/1998 | Jordan et al. |
| RE35,863 E | 7/1998 | Sachdeva et al. |
| 5,779,470 A | 7/1998 | Kussick |
| 5,791,897 A | 8/1998 | Wildman |
| 5,810,583 A | 9/1998 | Doyle |
| 5,820,371 A | 10/1998 | Forster |
| 5,829,972 A | 11/1998 | Farzin-Nia |
| 5,829,975 A | 11/1998 | Gold |
| 5,857,849 A | 1/1999 | Kurz |
| 5,871,350 A | 2/1999 | Clark et al. |
| 5,879,157 A | 3/1999 | Schue |
| 5,885,073 A | 3/1999 | Kussick |
| 5,885,074 A | 3/1999 | Hanson |
| 5,890,891 A | 4/1999 | Doyle |
| 5,908,293 A | 6/1999 | Voudouris |
| 5,915,550 A | 6/1999 | Gartz |
| 6,036,489 A | 3/2000 | Brosius |
| 6,053,458 A | 4/2000 | Meyer |
| 6,053,729 A | 4/2000 | Brehm et al. |
| 6,053,759 A | 4/2000 | Kunert et al. |
| 6,071,119 A | 6/2000 | Christoff et al. |
| 6,086,364 A | 7/2000 | Brunson |
| 6,109,916 A | 8/2000 | Wilcko et al. |
| 6,123,544 A | 9/2000 | Cleary |
| 6,126,441 A | 10/2000 | Tenti |
| 6,142,775 A | 11/2000 | Hansen et al. |
| 6,162,051 A | 12/2000 | Brehm et al. |
| 6,190,165 B1 | 2/2001 | Andreiko et al. |
| 6,193,508 B1 | 2/2001 | Georgakis |
| 6,206,690 B1 | 3/2001 | Vargas |
| 6,217,322 B1 | 4/2001 | Kesling |
| 6,220,857 B1 | 4/2001 | Abels |
| 6,227,849 B1 | 5/2001 | Brehm et al. |
| 6,234,792 B1 | 5/2001 | DeVincenzo |
| 6,264,469 B1 | 7/2001 | Moschik |
| 6,276,930 B1 | 8/2001 | Pozzi |
| 6,280,185 B1 | 8/2001 | Palmer et al. |
| 6,302,688 B1 | 10/2001 | Jordan et al. |
| 6,347,939 B2 | 2/2002 | Abels |
| 6,354,834 B2 | 3/2002 | Kanomi et al. |
| 6,358,043 B1 | 3/2002 | Mottate et al. |
| 6,358,046 B1 | 3/2002 | Brehm et al. |
| 6,361,314 B1 | 3/2002 | Garton, Jr. |
| 6,368,105 B1 | 4/2002 | Voudouris et al. |
| 6,371,760 B1 | 4/2002 | Zavilenski et al. |
| 6,394,798 B1 | 5/2002 | Huff et al. |
| 6,428,314 B1 * | 8/2002 | Jones et al. ................... 433/17 |
| 6,461,157 B1 | 10/2002 | Kussick |
| 6,478,579 B1 | 11/2002 | Brusse |
| 6,491,519 B1 | 12/2002 | Clark et al. |
| 6,506,049 B2 | 1/2003 | Hanson |
| 6,582,226 B2 | 6/2003 | Jordan et al. |
| 6,592,366 B2 | 7/2003 | Triaca et al. |
| 6,607,383 B2 | 8/2003 | Abels et al. |
| 6,616,445 B2 | 9/2003 | Abels et al. |
| 6,655,957 B2 | 12/2003 | Abels et al. |
| 6,655,958 B2 | 12/2003 | Abels et al. |
| 6,656,767 B1 | 12/2003 | King et al. |
| 6,659,766 B2 | 12/2003 | Abels et al. |
| 6,659,767 B2 | 12/2003 | Abels et al. |
| 6,663,385 B2 | 12/2003 | Tepper |
| 6,668,834 B1 | 12/2003 | Zikria |
| 6,695,612 B2 | 2/2004 | Abels et al. |
| 6,705,862 B2 | 3/2004 | Schultz |
| 6,709,268 B2 | 3/2004 | Pospisil et al. |
| 6,733,286 B2 | 5/2004 | Abels et al. |
| 6,769,910 B1 | 8/2004 | Pantino |
| 6,776,613 B2 | 8/2004 | Orikasa |
| 6,776,614 B2 | 8/2004 | Wiechmann et al. |
| 6,846,178 B2 | 1/2005 | Freeman, Jr. et al. |
| 6,863,528 B2 | 3/2005 | Lin |
| 6,877,982 B2 | 4/2005 | Williams |
| 6,893,257 B2 | 5/2005 | Kelly |
| 6,903,262 B2 | 6/2005 | Blersch |
| 6,910,884 B2 | 6/2005 | Kelly et al. |
| 6,913,459 B2 | 7/2005 | Fukutomi |
| 7,001,179 B2 | 2/2006 | Devincenzo |
| 7,025,591 B1 | 4/2006 | Kesling |
| 7,033,170 B2 | 4/2006 | Cordato |
| 7,033,171 B2 | 4/2006 | Wilkerson |
| 7,055,908 B1 | 6/2006 | Williams |
| 7,074,037 B2 | 7/2006 | Macchi |
| 7,094,052 B2 | 8/2006 | Abels et al. |
| 7,140,875 B2 | 11/2006 | Lai et al. |
| 7,151,541 B2 | 12/2006 | Seder |
| 7,153,130 B2 | 12/2006 | Christoff |
| 7,210,927 B2 | 5/2007 | Abels et a |
| 7,234,935 B2 | 6/2007 | Abels et al. |
| 7,247,018 B2 | 7/2007 | Freeman, Jr. et al. |
| 7,258,545 B2 | 8/2007 | Hotta |
| 7,267,545 B2 | 9/2007 | Oda |
| 7,306,458 B1 | 12/2007 | Lu et al. |
| 7,416,408 B2 | 8/2008 | Farzin-Nia et al. |
| 7,621,743 B2 | 11/2009 | Bathen et al. |
| 7,695,277 B1 | 4/2010 | Stevens |
| 7,704,072 B2 | 4/2010 | Damon |
| 7,780,443 B2 | 8/2010 | Hagelganz et al. |
| 7,811,087 B2 | 10/2010 | Wiechmann et al. |
| 7,850,451 B2 | 12/2010 | Wiechmann et al. |
| 7,909,603 B2 | 3/2011 | Oda |
| 7,959,437 B2 | 6/2011 | Zakhem et al. |
| 7,963,768 B2 | 6/2011 | Hilliard |
| 8,251,697 B2 * | 8/2012 | Smith et al. ................... 433/17 |
| 8,376,739 B2 | 2/2013 | Dupray et al. |
| 8,485,816 B2 | 7/2013 | Macchi |
| 8,573,971 B2 | 11/2013 | Stevens |
| 8,585,399 B2 * | 11/2013 | Smith et al. ................... 433/17 |
| 2001/0036615 A1 | 11/2001 | Binder |
| 2002/0025502 A1 | 2/2002 | Williams |
| 2002/0110778 A1 | 8/2002 | Abels et al. |
| 2002/0187452 A1 | 12/2002 | Abels et al. |
| 2003/0049582 A1 | 3/2003 | Abels et al. |
| 2003/0064344 A1 | 4/2003 | Vazquez |
| 2003/0088261 A1 | 5/2003 | Schraga |
| 2003/0096209 A1 | 5/2003 | Sugiyama et al. |
| 2003/0143509 A1 | 7/2003 | Kopelman et al. |
| 2004/0244149 A1 | 12/2004 | Anscher |
| 2004/0259048 A1 | 12/2004 | Balabanovsky |
| 2005/0069833 A1 | 3/2005 | Chikami |
| 2005/0244777 A1 * | 11/2005 | Schultz ................... 433/17 |
| 2006/0014116 A1 | 1/2006 | Maijer et al. |
| 2006/0046224 A1 | 3/2006 | Sondhi et al. |
| 2006/0063123 A1 | 3/2006 | Cleary et al. |
| 2006/0099544 A1 | 5/2006 | Lai et al. |
| 2006/0099545 A1 | 5/2006 | Lai et al. |
| 2006/0199137 A1 | 9/2006 | Abels et al. |
| 2006/0228662 A1 | 10/2006 | Lokar et al. |
| 2006/0228664 A1 | 10/2006 | Castner et al. |
| 2006/0246392 A1 | 11/2006 | Vigolo |
| 2006/0252002 A1 | 11/2006 | Hanson |
| 2006/0257810 A1 | 11/2006 | Maijer et al. |
| 2006/0263737 A1 | 11/2006 | Oda |
| 2006/0269889 A1 | 11/2006 | Voudouris |
| 2007/0054231 A1 | 3/2007 | Manemann et al. |
| 2007/0092849 A1 | 4/2007 | Cosse |
| 2007/0166658 A1 | 7/2007 | Voudouris |
| 2007/0207436 A1 | 9/2007 | Tan et al. |
| 2007/0224569 A1 | 9/2007 | Oda |
| 2007/0243497 A1 | 10/2007 | Voudouris |
| 2007/0248926 A1 | 10/2007 | Lai et al. |
| 2007/0256694 A1 | 11/2007 | Kussick |
| 2007/0264606 A1 | 11/2007 | Muha et al. |
| 2007/0281269 A1 | 12/2007 | Forster |
| 2008/0014544 A1 | 1/2008 | Nucera |
| 2008/0128297 A1 | 6/2008 | Rose |

(56) References Cited

U.S. PATENT DOCUMENTS

| | | |
|---|---|---|
| 2008/0131831 A1 | 6/2008 | Abels et al. |
| 2008/0138759 A1 | 6/2008 | Kravitz et al. |
| 2008/0160474 A1 | 7/2008 | Wolf et al. |
| 2008/0182219 A1 | 7/2008 | Spalty |
| 2008/0223377 A1 | 9/2008 | Kussick |
| 2008/0227047 A1 | 9/2008 | Lowe et al. |
| 2008/0268398 A1 | 10/2008 | Cantarella |
| 2009/0004617 A1 | 1/2009 | Oda et al. |
| 2009/0004618 A1 | 1/2009 | Oda et al. |
| 2009/0004619 A1 | 1/2009 | Oda et al. |
| 2009/0042160 A1 | 2/2009 | Ofir |
| 2009/0162807 A1 | 6/2009 | Hagelganz et al. |
| 2009/0291404 A1 | 11/2009 | Oda |
| 2009/0325118 A1 | 12/2009 | Lewis et al. |
| 2010/0003632 A1 | 1/2010 | Ruiz Diaz et al. |
| 2010/0062387 A1 | 3/2010 | Hilliard |
| 2010/0129765 A1 | 5/2010 | Mohr et al. |
| 2010/0159411 A1 | 6/2010 | Oda |
| 2010/0178629 A1 | 7/2010 | Oda et al. |
| 2010/0196840 A1 | 8/2010 | Lai et al. |
| 2010/0203463 A1 | 8/2010 | Huff |
| 2010/0261131 A1 | 10/2010 | Ruiz-Vela et al. |
| 2010/0279247 A1 | 11/2010 | Kesling |
| 2010/0285420 A1 | 11/2010 | Oda |
| 2010/0285421 A1 | 11/2010 | Heiser |
| 2010/0304321 A1 | 12/2010 | Patel |
| 2011/0014583 A1 | 1/2011 | Romano et al. |
| 2011/0020762 A1 | 1/2011 | Kanomi et al. |
| 2011/0039224 A1 | 2/2011 | Cosse |
| 2011/0076633 A1 | 3/2011 | Bryant |
| 2011/0081622 A1 | 4/2011 | Mashouf |
| 2011/0086322 A1 | 4/2011 | Baron et al. |
| 2011/0123942 A1 | 5/2011 | Rudman et al. |
| 2011/0165532 A1 | 7/2011 | Benvegnu' et al. |
| 2011/0287378 A1 | 11/2011 | Dupray et al. |
| 2012/0070797 A1 | 3/2012 | Edgren |
| 2013/0189639 A1 | 7/2013 | Dupray et al. |
| 2013/0280668 A1 | 10/2013 | Upchurch, Jr. et al. |
| 2013/0280670 A1 | 10/2013 | Edgren |
| 2013/0302745 A1 | 11/2013 | Aldo |
| 2013/0309624 A1 | 11/2013 | Smith et al. |
| 2013/0309625 A1 | 11/2013 | Macchi et al. |

FOREIGN PATENT DOCUMENTS

| | | |
|---|---|---|
| EP | 0317098 | 5/1989 |
| EP | 0379668 | 8/1990 |
| EP | 0389223 | 9/1990 |
| EP | 0397533 | 11/1990 |
| EP | 0588961 | 3/1994 |
| EP | 0624354 | 11/1994 |
| EP | 0875211 | 11/1998 |
| EP | 1332727 | 8/2003 |
| EP | 1359859 | 11/2003 |
| ES | 2130174 | 7/1999 |
| FR | 2497657 | 7/1982 |
| FR | 2887135 | 12/2006 |
| JP | S64-25847 | 1/1989 |
| JP | H01-160547 | 6/1989 |
| JP | H02-147112 | 12/1990 |
| JP | H03-21236 | 1/1991 |
| JP | H06-507803 | 9/1994 |
| JP | 2579431 | 2/1997 |
| JP | 11-276504 | 10/1999 |
| JP | 2003-102749 | 4/2003 |
| WO | WO 91/07925 | 6/1991 |
| WO | WO 92/00041 | 1/1992 |
| WO | WO 92/20296 | 11/1992 |
| WO | WO 2004/039276 | 5/2004 |

OTHER PUBLICATIONS

U.S. Appl. No. 11/123,470, filed May 5, 2005, Wilson.
U.S. Appl. No. 13/199,828, filed Sep. 9, 2011, Rudman et al.
U.S. Appl. No. 13/506,513, filed Apr. 23, 2012, Rudman et al.
3M Unitek Corporation Catalog, 1990, pp. 1-1, 1-3, 3-7, Figs. A, B.
"Buccal Tube," Sankin, printed Apr. 1, 2004, 7 pages.
"Direct Bond Tubes," American Orthodontics, New Products Catalog, 2005, p. 76.
"Focus on Brackets," Orthodontic Products, Mar. 2005, pp. 1-2.
Ortho Organizers, Inc. Advertisement, "Journal of Clinical Orthodontics," Sep. 1989, 3 pages.
Victory Series Appliance System, Mastering the Art of Orthodontic Application, 3M Unitek Dental Products Division, 1998, 4 pages.
Epstein, "Bi-Dimensional Orthos Treatment: Benefits and Rationale of Differential Bracket-Slot Sizes," Clinical Impressions, 1998, vol. 7(3), 6 pages.
Ricketts, "Provocations and Perceptions in Cranio-Facial Orthopedics," RMO, Inc., Denver, CO, USA, 1989, cover and pp. 982-1021.
International Search Report mailed Apr. 1, 2008 for PCT application PCT/US2007/077922, filed Sep. 7, 2007.
Written Opinion mailed Apr. 1, 2008 for PCT application PCT/US2007/077922, filed Sep. 7, 2007.
International Preliminary Report on Patentability for International (PCT) Patent Application No. PCT/US2007/077922, mailed Mar. 19, 2009.
Official Action for U.S. Appl. No. 11/852,057, mailed May 7, 2009.
Official Action for U.S. Appl. No. 11/852,057, mailed Jan. 22, 2010.
Official Action for U.S. Appl. No. 11/852,057, mailed Jun. 4, 2010.
Official Action for U.S. Appl. No. 11/852,057, mailed Nov. 16, 2010.
Official Action for U.S. Appl. No. 11/852,057, mailed Jun. 3, 2011.
Official Action for U.S. Appl. No. 11/852,057, mailed Sep. 29, 2011 29 pages.
Official Action for U.S. Appl. No. 13/595,548, mailed Jan. 17, 2013, 6 pages.
Notice of Allowance for U.S. Appl. No. 13/595,548, mailed Jun. 4, 2013, 8 pages.

* cited by examiner

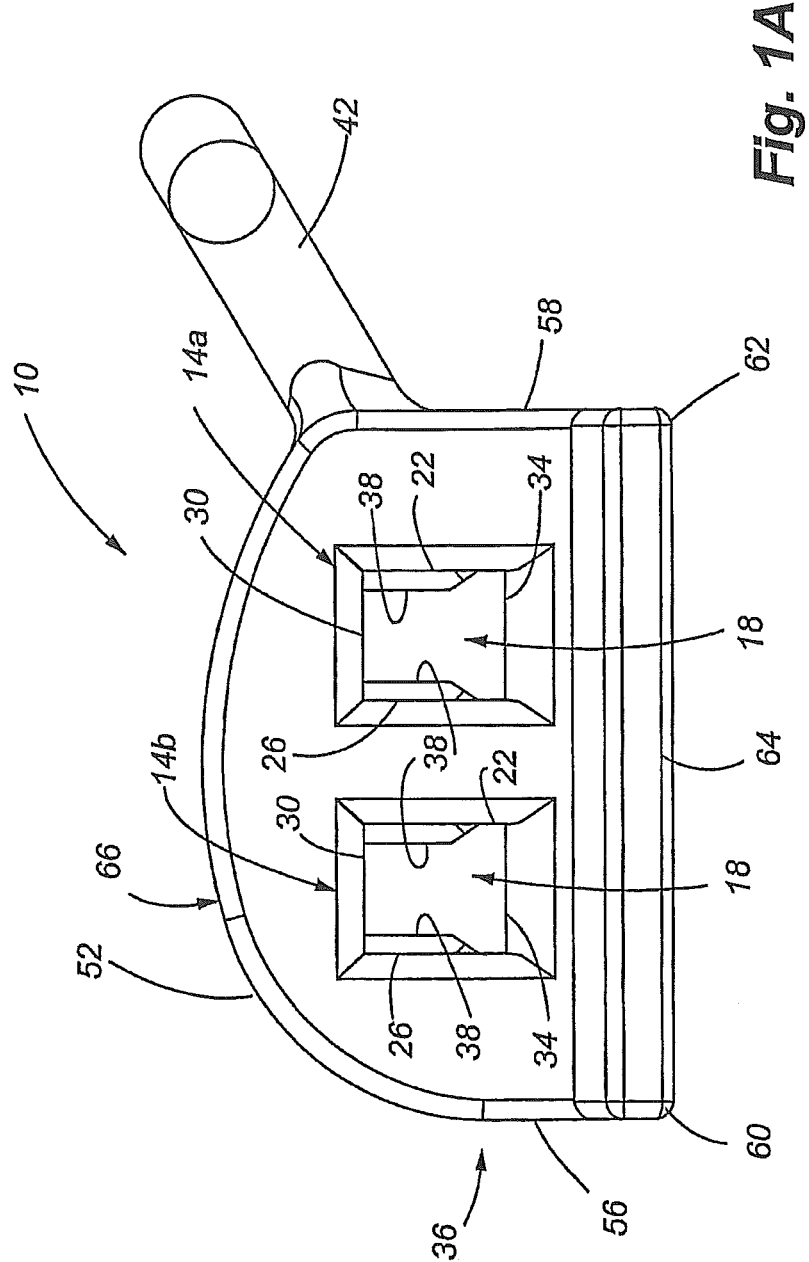

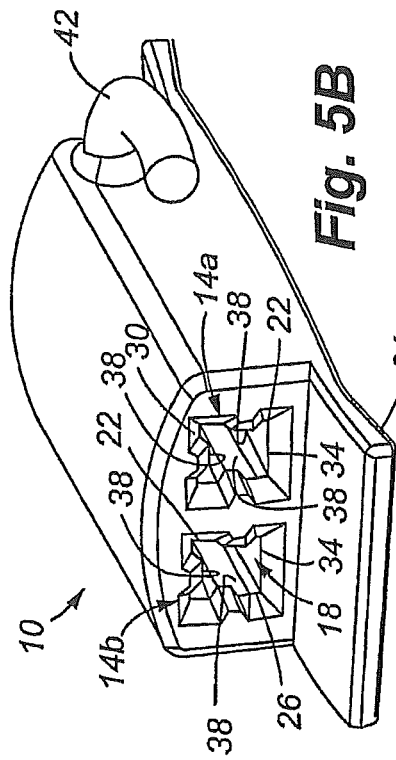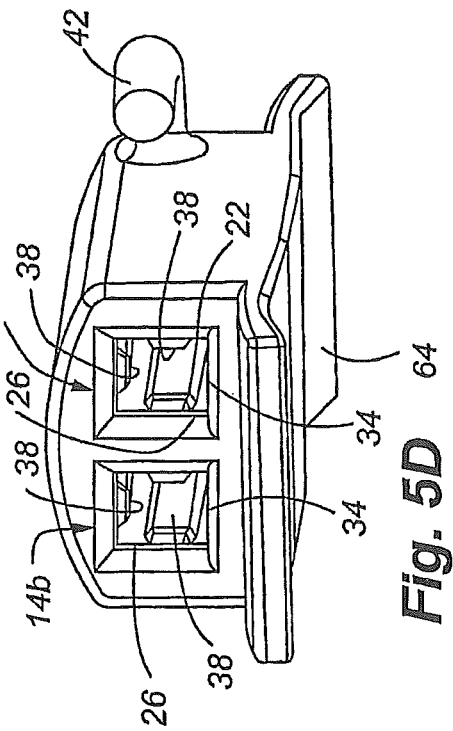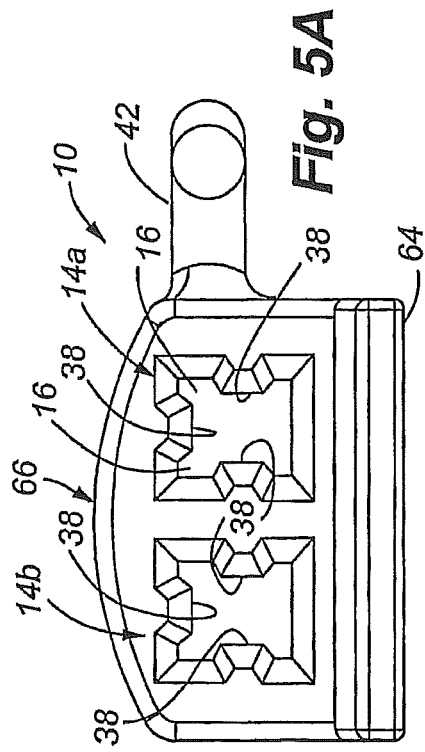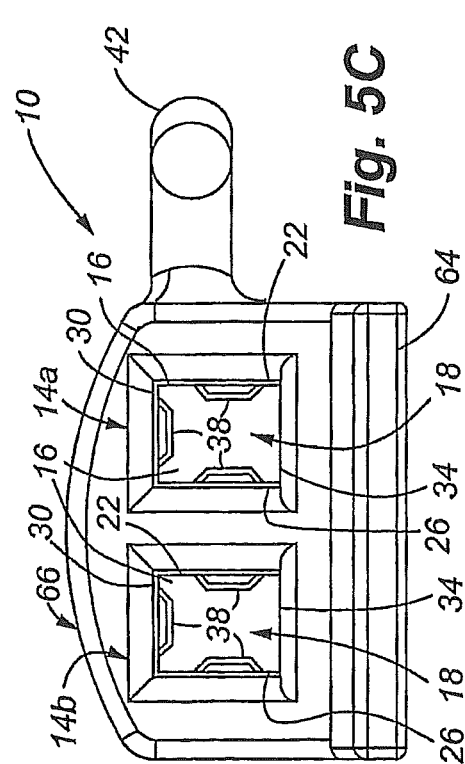

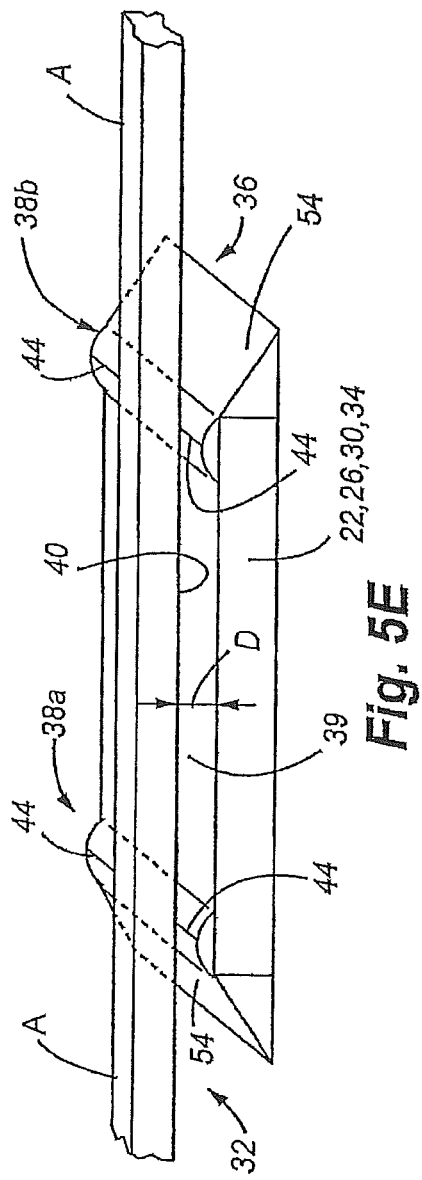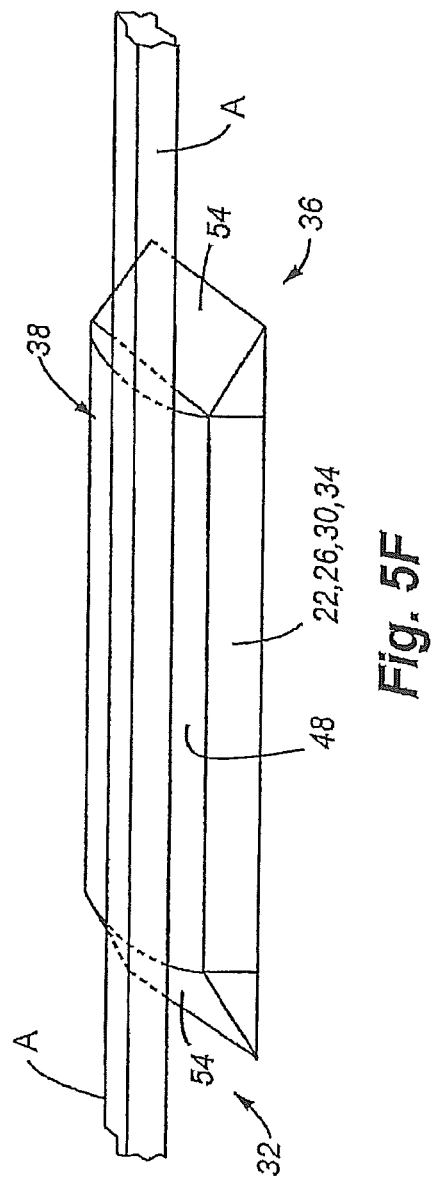
Fig. 5E
Fig. 5F

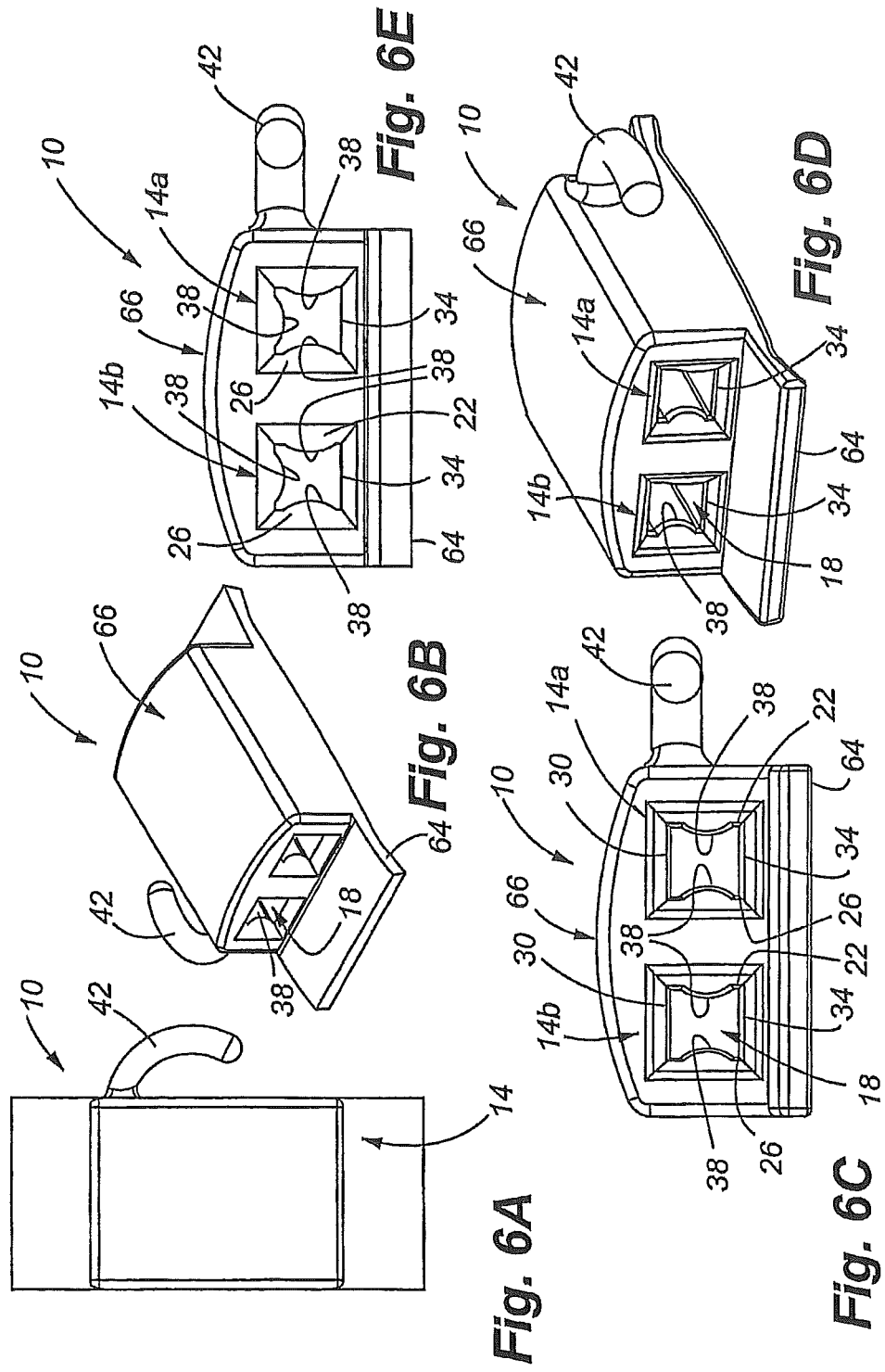

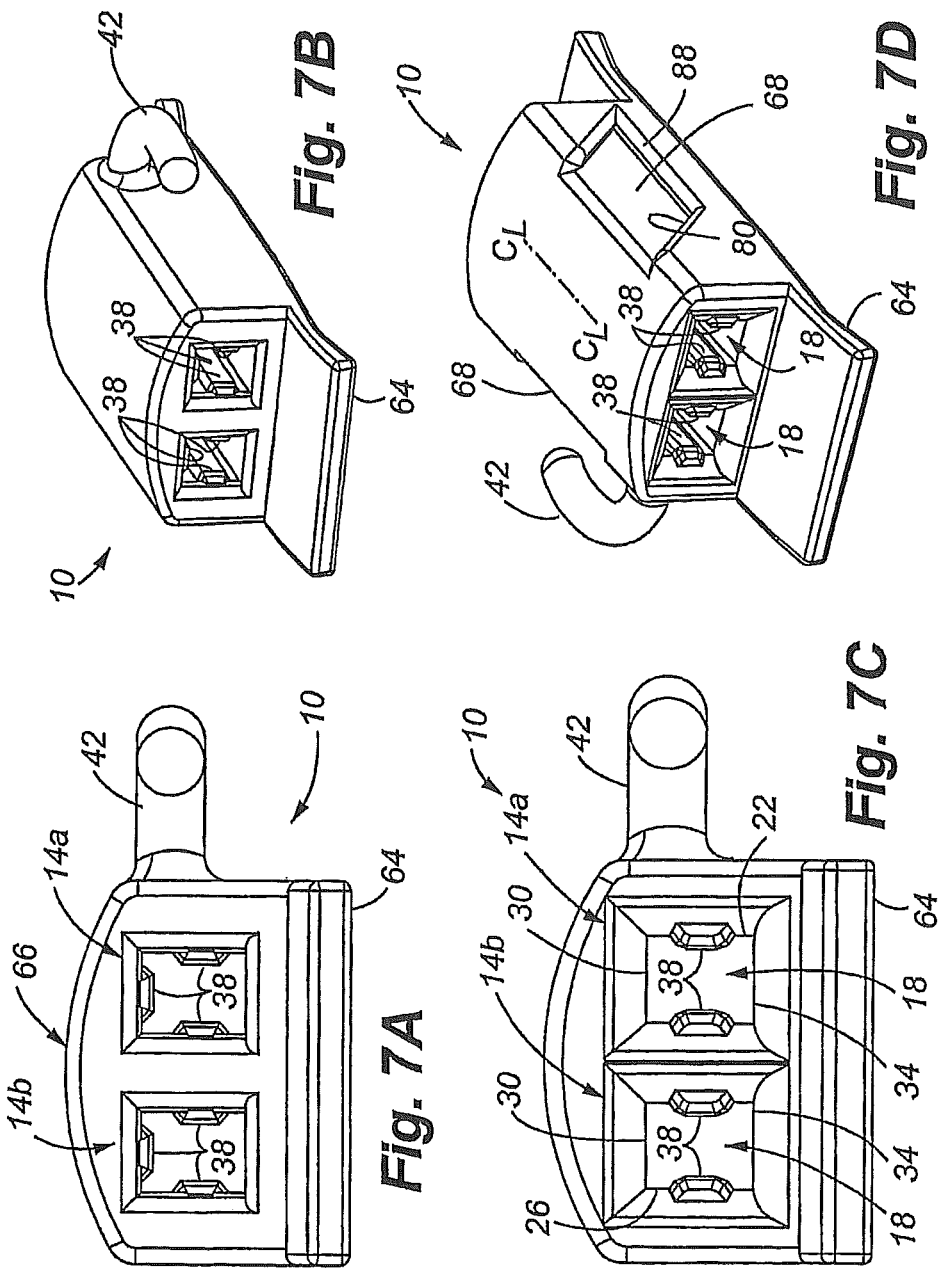

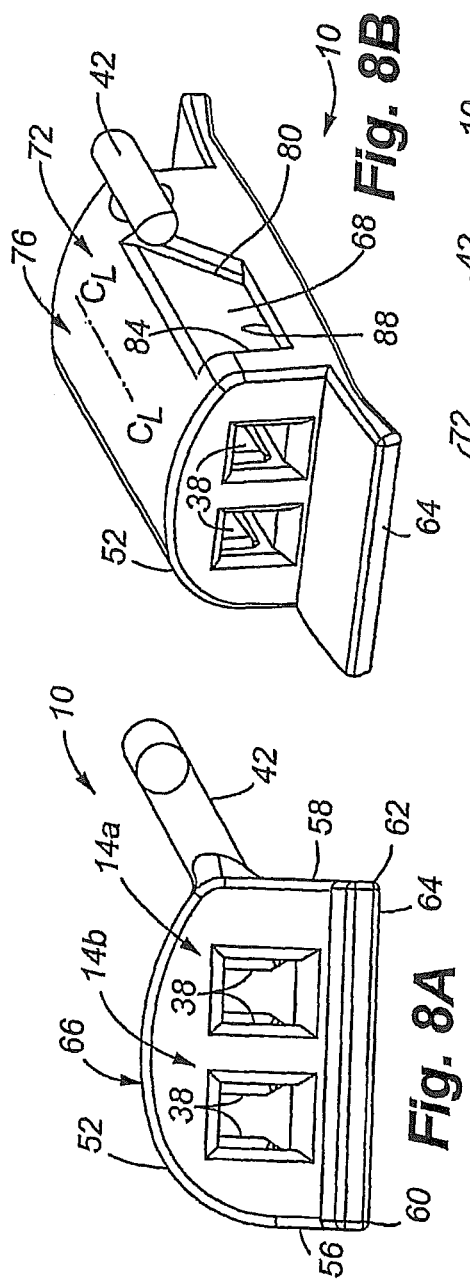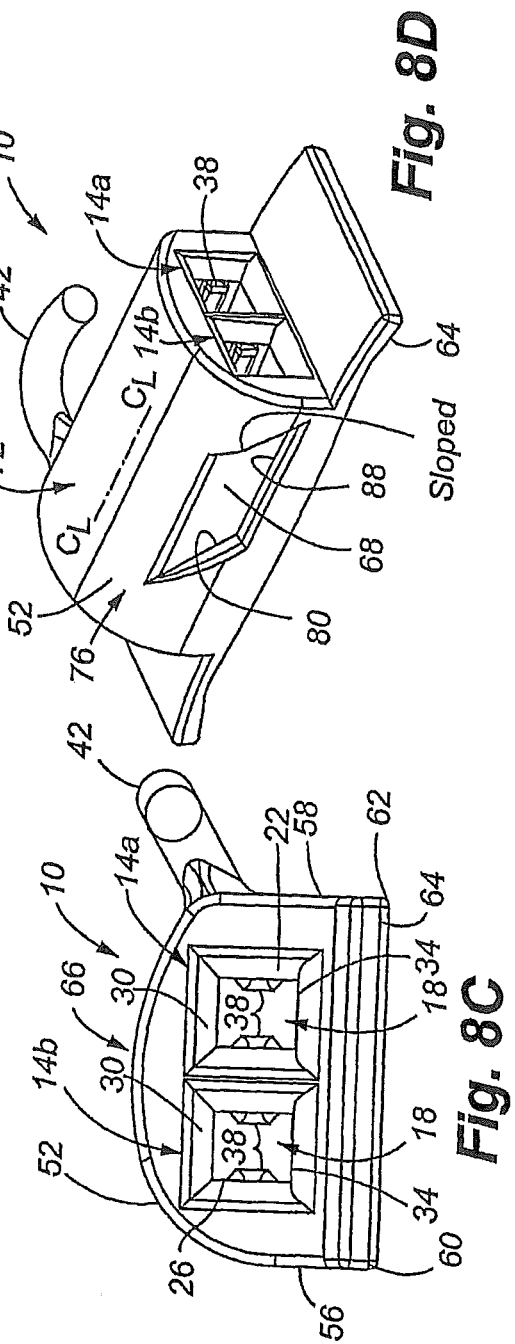

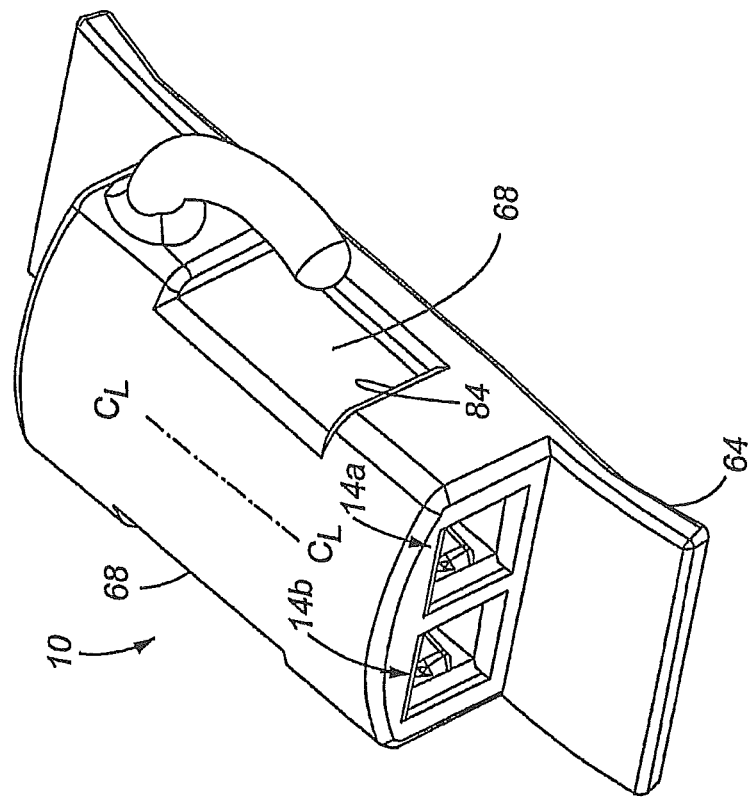
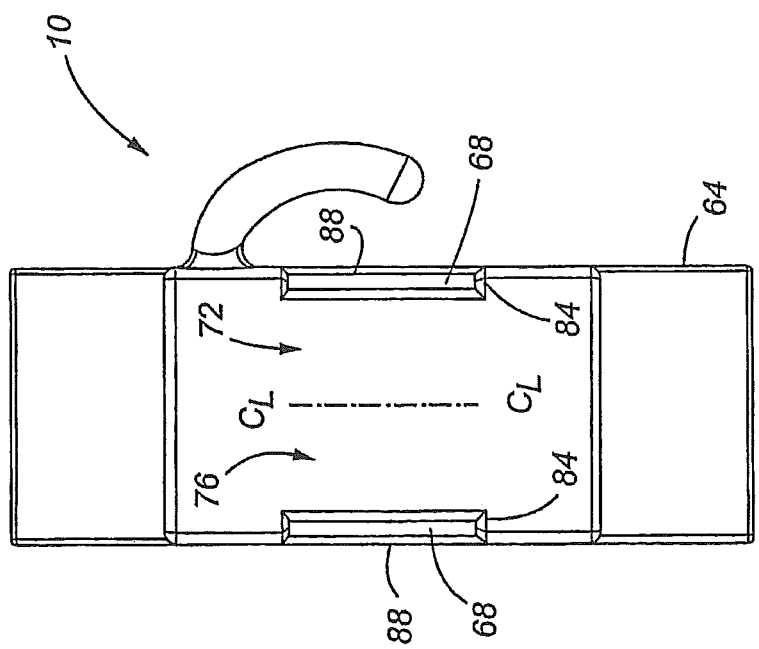
Fig. 9B
Fig. 9A

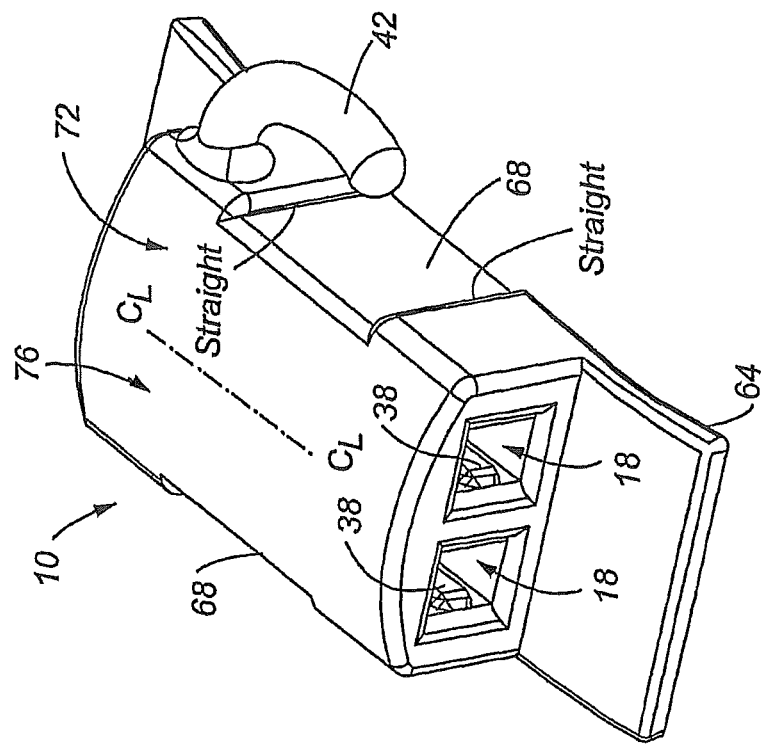
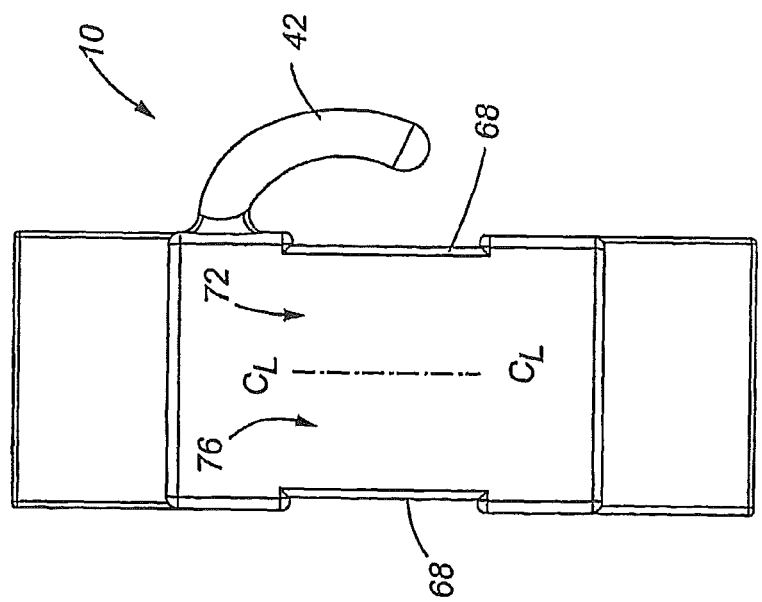
Fig. 10B
Fig. 10A

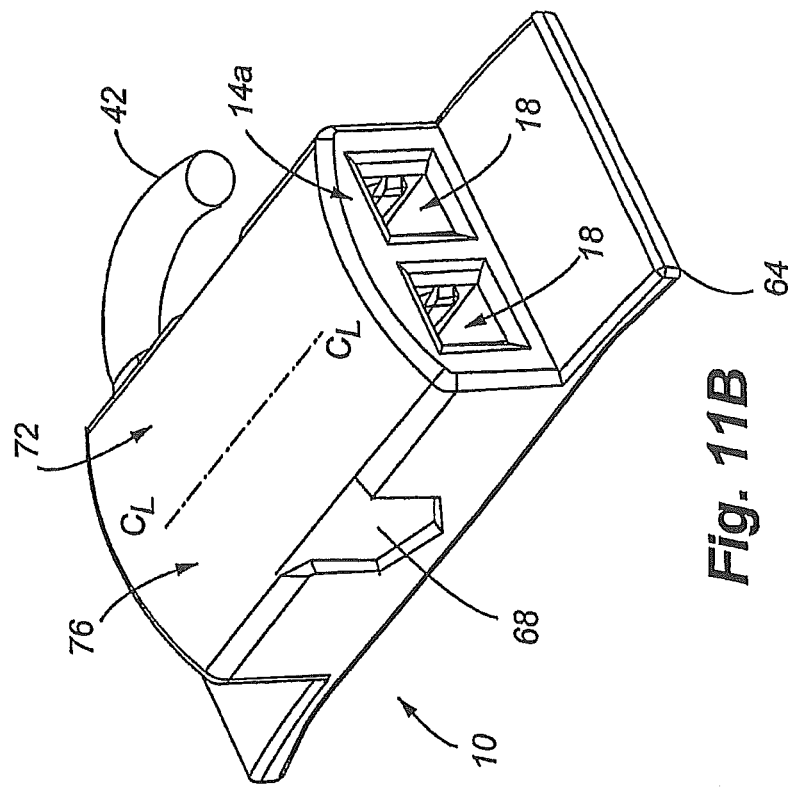
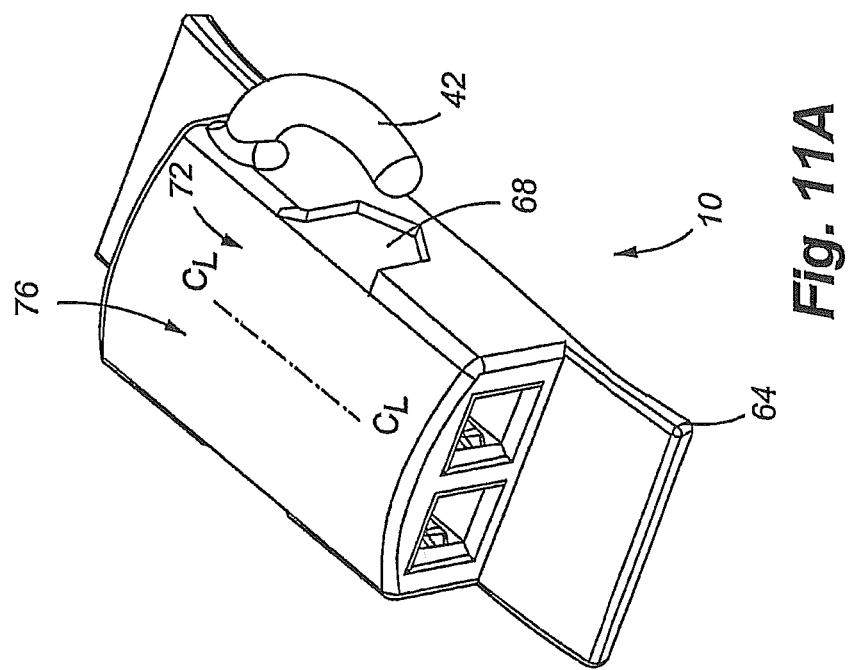
Fig. 11A
Fig. 11B

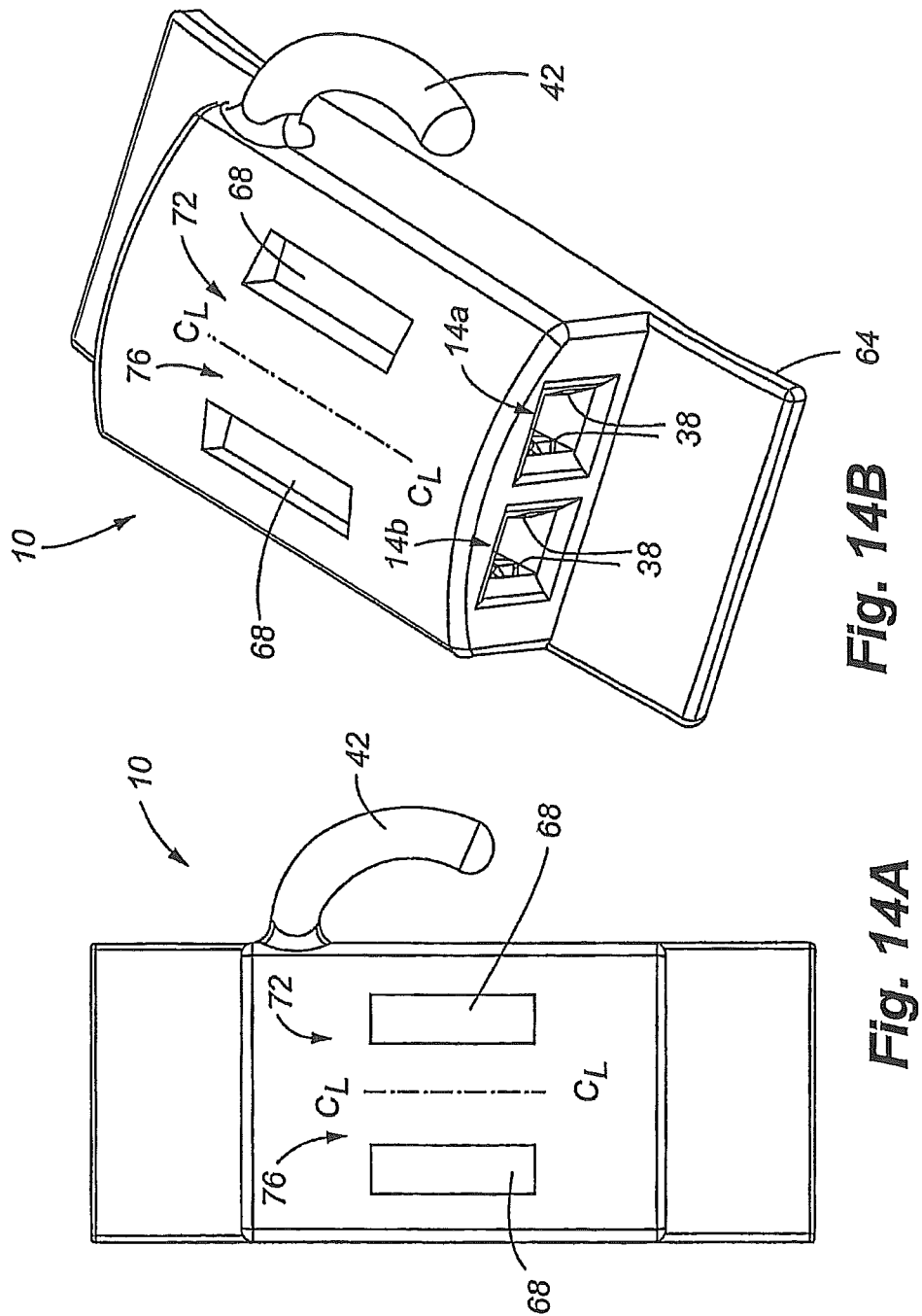

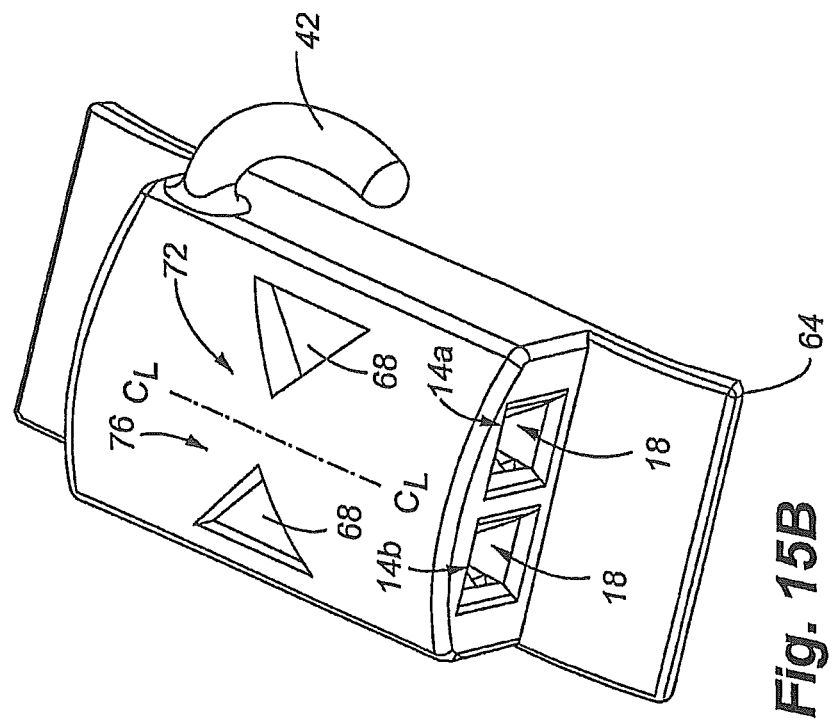
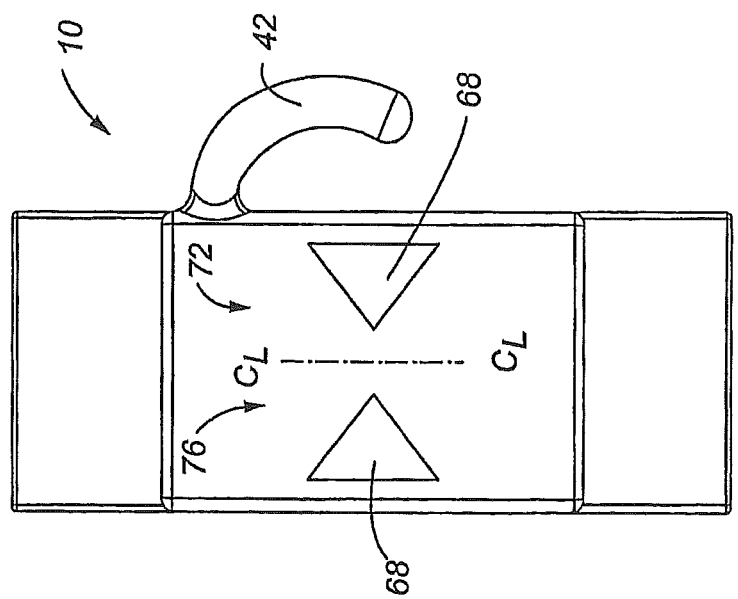
Fig. 15A
Fig. 15B

REDUCED-FRICTION BUCCAL TUBE AND METHOD OF USE

CROSS-REFERENCE TO RELATED APPLICATION

This application is a continuation of U.S. patent application Ser. No. 13/595,548, filed Aug. 27, 2012, which is a continuation of U.S. patent application Ser. No. 11/852,057, filed Sep. 7, 2007 (now U.S. Pat. No. 8,251,697, issued on Aug. 28, 2012), and claims the benefit of U.S. Provisional Application No. 60/824,891 filed on Sep. 7, 2006, the entire disclosure of each application is incorporated herein by reference in their entirety.

FIELD OF THE INVENTION

The present invention is directed to an orthodontic appliance, and more particularly, to a buccal tube and methods of use for the buccal tube.

BACKGROUND

The following text should not be construed as an admission of knowledge in the prior art. Furthermore, citation or identification of any document in this application is not an admission that such document is available as prior art to the present invention, or that any reference forms a part of the common general knowledge in the art.

A buccal tube is an appliance used by orthodontists during a phase of treatment to correct malpositioned teeth. The buccal tube is a device attached to a patient's tooth for orthodontic treatment in which the buccal or cheek-facing side of the appliance includes a structure having an opening that is typically suited for receiving another orthodontic hardware member, such as an archwire, lip bumper, facebow, headgear appliance, etc.

For buccal tubes used with archwires, existing buccal tubes have difficulties associated with the development of friction between the buccal tube and the archwire inserted within the archwire slot of the buccal tube. This type of friction (also referred to herein as "binding friction") tends to cause binding between the archwire and the buccal tube. Accordingly, there is a need to provide a buccal tube that reduces the amount of friction developed between the archwire slot of the buccal tube and the archwire.

Existing buccal tubes also have a shape that often irritates the inside of the patient's cheek because the edge of the buccal tube repeatedly rubs against the cheek tissue. Thus, it would be advantageous to provide a buccal tube that improves comfort of the appliance so that the buccal tube is less irritating to the patient, thereby improving patient satisfaction and cooperation.

Finally, orthodontists face a number of difficulties in applying orthodontic appliances to teeth because of the relatively small size of the appliances and the inherent problems associated with working within the confines of a patient's mouth. Prior patents at least partially directed to installation features include U.S. Pat. Nos. 6,206,690 and 6,893,257, the contents of which are incorporated herein by reference in their entirety. Also incorporated by reference in its entirety is U.S. Patent Application Publication No. 2006/0046224. Although these documents include some features for aiding the installation of an orthodontic appliance, there remains a need to provide improved appliance features to facilitate easier and more accurate placement of the appliance on the patient's tooth by the orthodontist.

SUMMARY

The shortcomings of the prior art discussed above are addressed by the various embodiments of the present invention. It is to be understood that the present invention includes a variety of different versions or embodiments, and this Summary is not meant to be limiting or all-inclusive. This Summary provides some general descriptions of some of the embodiments, but may also include some more specific descriptions of certain embodiments.

In accordance with embodiments of the present invention, an appliance comprises a base designed for at least one of direct or indirect attachment to a tooth, and at least one archwire slot or appliance slot of some kind that is interconnected to or integral with the base.

In accordance with embodiments of the present invention, a reduced friction buccal tube is provided. The reduced friction feature keeps the archwire from dragging or causing friction in the archwire slot, especially in the corners of the openings of the archwire slot. In at least one embodiment, the reduced friction part of the archwire slot is a protrusion that limits the amount of surface area that an archwire (of any shape) is touching in the length of the archwire slot; however the clinical control remains the same because the archwire slot of the buccal tube maintains contact with the archwire for substantially the full mesial to distal length of the archwire slot. Embodiments of the present invention further comprise rounded features for improving patient comfort, as well as features for facilitating easier installation of the appliance on the patient's tooth.

Thus, in accordance with embodiments of the present invention, an orthodontic appliance for cooperating with an archwire is provided, the appliance comprising, a base and at least one archwire slot associated with the base, the archwire slot comprising a first aperture and a second aperture defining a passageway between the first and second apertures, wherein the passageway is adapted for receiving the archwire, and wherein at least a portion of an interior surface of the archwire slot proximate the passageway comprises a friction-reducing feature. In accordance with embodiments of the present invention, the friction-reducing feature comprises at least one projection. In accordance with embodiments of the present invention, the friction-reducing feature comprises at least a second projection longitudinally aligned with the first projection. In at least one embodiment of the present invention, the archwire slot comprises an exterior surface wherein at least a portion of the exterior surface is rounded. In addition, the exterior surface may comprise a substantially planar surface adjacent an occlusal-base edge. Also, the exterior surface may comprise a substantially planar surface adjacent a gingival-base edge. In accordance with embodiments of the present invention, the appliance may further comprise a pair of receptacles having a tool receiving surface inset from the exterior surface, at least one of the pair of receptacles located on an occlusal side of the exterior surface, and another of the pair of receptacles located on a gingival side of the exterior surface. In accordance with embodiments of the present invention, the appliance may comprise at least one receptacle in the exterior surface, the receptacle comprising a tool receiving surface adapted for cooperating with a placement tool, the tool receiving surface comprising a single projection and a single indentation. In accordance with embodiments of the present invention, the appliance may comprise at least a second receptacle in the exterior surface, the second receptacle comprising a tool receiving surface adapted for cooperating with the placement tool, the tool receiving surface comprising a single projection and a single cavity or indentation. In accordance with embodiments of the present invention, the appliance may comprise at least one receptacle in the exterior surface, the receptacle for receiving a tool that applies a force directed outward from a center of the receptacle. In accordance with embodiments of the present invention, the appliance may comprise at least one of (a) a second archwire slot and (b) an auxiliary tube.

In another embodiment of the invention, an orthodontic appliance is provided, the appliance comprising a base and at least one archwire/appliance slot/tube associated with the base, the archwire/appliance slot/tube including an exterior surface and a pair of receptacles having a tool receiving surface inset from the exterior surface. In accordance with at least one embodiment of the present invention, at least one of the pair of receptacles is located on an occlusal side of a longitudinally-oriented centerline of the exterior surface, and another of the pair of receptacles located on a gingival side of the longitudinally-oriented centerline of the exterior surface. In accordance with embodiments of the present invention, the archwire/appliance slot/tube comprises a first aperture and a second aperture defining a passageway between the first and second apertures, wherein the passageway is adapted for receiving an archwire, and wherein at least a portion of an interior surface of the buccal tube proximate the passageway comprises a friction-reducing feature. At least a portion of the exterior surface may be rounded.

In another embodiment of the invention, a buccal tube for attachment to a tooth is provided, the buccal tube comprising:
 a base;
 at least one archwire slot associated with said base, the archwire slot including interior sides comprising a gingival side, an occlusal side, a buccal side, and a lingual side, wherein a plurality of the gingival, occlusal, buccal and lingual sides comprise a friction reducing feature, wherein said friction reducing feature comprises at least one of:
  (a) a plurality of longitudinally aligned projections; and
  (b) a longitudinally extending projection.
The archwire slot may further comprise an exterior surface and a pair of receptacles having a tool receiving surface inset from said exterior surface, at least one of said pair of receptacles located on an occlusal side of a longitudinally-oriented centerline of said archwire slot, and another one of said pair of receptacles located on a gingival side of the longitudinally oriented centerline of said archwire slot, the pair of receptacles including a mesial edge trending in a mesial to distal direction from a buccal to a lingual side of the receptacle, wherein at least a portion of said exterior surface is rounded, wherein said exterior surface comprises a substantially planar surface adjacent an occlusal-base edge, and wherein said exterior surface comprises a substantially planar surface adjacent a gingival-base edge.

The present invention contemplates use of alternate features than those described, but encompassed by the scope of the invention. Accordingly, an orthodontic appliance is provided for cooperating with an archwire, the appliance comprising structure for defining a mesial-distally oriented chamber adapted for receiving the archwire, the structure for defining the mesial-distally oriented chamber comprising a way for reducing friction between the structure for defining the mesial-distally oriented chamber and the archwire.

An orthodontic appliance for cooperating with an archwire is provided, the appliance comprising: means for defining a mesial-distally oriented chamber adapted for receiving the archwire and including an exterior surface buccally enclosing the chamber, the means for defining comprising one or more means for reducing friction with the archwire, the one or more means for reducing friction located along interior sides of the means for defining, wherein the one or more means for reducing friction contacts one or more portions of the archwire along a longitudinal length of the mesial-distally oriented chamber, and wherein the one or more means for reducing friction are located along at least two opposite sides of the chamber.

In addition to the foregoing, the present invention further comprises methods of adjusting a position of a tooth. At least one method comprising:
 attaching a buccal tube to the tooth;
 directing an archwire into an archwire slot in the buccal tube, the archwire slot including a gingival side, an occlusal side, a buccal side, and a lingual side; and
 contacting an exterior surface of the archwire with friction reducing features located within the archwire slot, the friction reducing features comprising at least one of:
  (a) a plurality of projections residing along a longitudinal length of at least one of the gingival side, occlusal side, buccal side, and lingual side; and
  (b) a longitudinally extending projection residing along a longitudinal length of one or more of the gingival side, occlusal side, buccal side, and lingual side.
The attaching step may comprise engaging the buccal tube using an installation tool, an exterior of the buccal tube comprising a pair of receptacles for receiving a portion of the installation tool.

A method of adjusting a tooth comprises grasping an appliance using an installation tool, such as tweezers, wherein the appliance comprises a base interconnected to or integral with an archwire/appliance slot/tube, the archwire/appliance slot/tube comprising a pair of receptacles for receiving a portion of the installation tool. The method further comprises advancing the installation tool into the patient's mouth with the appliance held in compression, and then contacting the appliance to a tooth of the patient. Other methods include treating a patient using an appliance and an archwire, wherein the appliance comprises an archwire/appliance slot/tube having a friction-reducing feature for cooperating with the archwire.

Other aspects of various embodiments not summarized here are also considered to form part of the present invention, either alone or in combination with other aspects.

As used herein, "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

It is to be noted that the term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

Various embodiments of the present invention are set forth in the attached figures and in the detailed description of the invention as provided herein and as embodied by the claims. It should be understood, however, that this Summary does not contain all of the aspects and embodiments of the present invention, is not meant to be limiting or restrictive in any manner, and that the invention as disclosed herein is and will be understood by those of ordinary skill in the art to encompass obvious improvements and modifications thereto.

Additional advantages of the present invention will become readily apparent from the following discussion, particularly when taken together with the accompanying drawings.

BRIEF DESCRIPTION OF THE DRAWINGS

FIG. 1A is a side elevation view of a distal end of an orthodontic appliance in accordance with embodiments of the present invention;

FIG. 5A is a side elevation view of a distal end of an orthodontic appliance in accordance with embodiments of the present invention;

FIG. 5B is a perspective view of the device shown in FIG. 5A;

FIG. 5C is a side elevation view of a distal end of an orthodontic appliance in accordance with embodiments of the present invention;

FIG. 5D is a perspective view of the device shown in FIG. 5C;

FIG. 5E is a depiction of one embodiment of a side of the appliance where a crown or ridge line is employed to contact an archwire so that the archwire does not contact the majority of the length of the side because the projections cause the archwire to be spaced apart from the surface of the side;

FIG. 5F is yet another embodiment of a longitudinally extending projection along a side of the appliance;

FIG. 6A is a plan view of an orthodontic appliance in accordance with embodiments of the present invention;

FIG. 6B is a perspective view of the device shown in FIG. 6A;

FIG. 6C is a side elevation view of a distal end of an orthodontic appliance in accordance with embodiments of the present invention;

FIG. 6D is a perspective view of the device shown in FIG. 6C;

FIG. 6E is a side elevation view of the distal end of the device shown in FIGS. 6A and 6B;

FIG. 7A is a side elevation view of a distal end of an orthodontic appliance in accordance with embodiments of the present invention;

FIG. 7B is a perspective view of the device shown in FIG. 7A;

FIG. 7C is a side elevation view of a distal end of an orthodontic appliance in accordance with embodiments of the present invention;

FIG. 7D is a perspective view of the device shown in FIG. 7C;

FIG. 8A is a side elevation view of a distal end of an orthodontic appliance in accordance with embodiments of the present invention;

FIG. 8B is a perspective view of the device shown in FIG. 8A;

FIG. 8C is a side elevation view of a distal end of an orthodontic appliance in accordance with embodiments of the present invention;

FIG. 8D is a perspective view of the device shown in FIG. 8C;

FIG. 9A is a plan view of an orthodontic appliance in accordance with embodiments of the present invention;

FIG. 9B is a perspective view of the device shown in FIG. 9A;

FIG. 10A is a plan view of an orthodontic appliance in accordance with embodiments of the present invention;

FIG. 10B is a perspective view of the device shown in FIG. 10A;

FIGS. 11A and 11B are perspective views of an orthodontic appliance in accordance with embodiments of the present invention;

FIG. 14A is a plan view of an orthodontic appliance in accordance with embodiments of the present invention;

FIG. 14B is a perspective view of the device shown in FIG. 14A;

FIG. 15A is a plan view of an orthodontic appliance in accordance with embodiments of the present invention;

FIG. 15B is a perspective view of the device shown in FIG. 15A; and

The drawings are not necessarily to scale, may include exaggerated features, and may depict one or more inventions.

DETAILED DESCRIPTION OF THE INVENTION

Referring now to FIG. 1A, and in accordance with at least one embodiment of one or more of the present inventions described herein, an orthodontic appliance in the form of a buccal tube 10 is shown, wherein the buccal tube 10 incorporates features to reduce the binding friction developed between the buccal tube 10 and a device inserted into the buccal tube 10. For example, the present invention includes buccal tubes 10 having at least one archwire slot 14 with friction reducing features for improved interaction with an archwire. The present invention is applicable to a buccal tube 10 having only one archwire slot 14, or to a buccal tube 10 having a plurality of archwire slots 14. In addition, as can appreciated by those skilled in the art, it is to be understood that the present invention is applicable to a buccal tube 10 that utilizes one or more archwire slots 14 in combination with other elongated openings, such as auxiliary tubes, headgear tubes and appliance slots. Accordingly, "archwire slot" is used to generally define an elongated opening that is adapted for receiving an archwire. However, as used herein, the more generic term "archwire/appliance slot/tube" means an elongated opening that is adapted for receiving either an archwire or some other type of appliance.

Figure 1B:
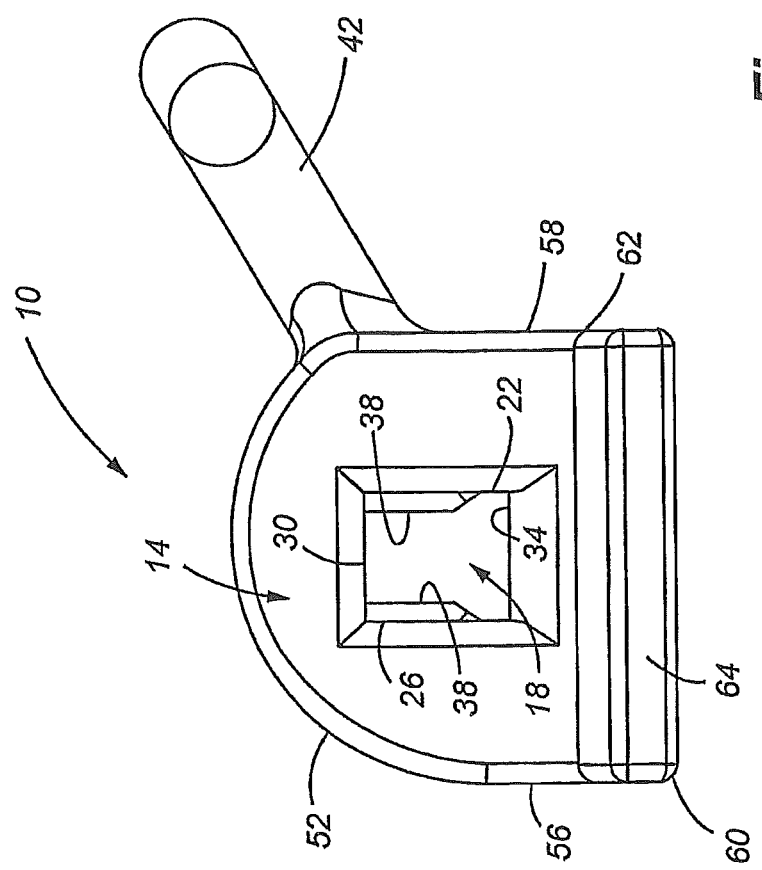
FIG. 1B is a side elevation view of a distal end of an orthodontic appliance in accordance with embodiments of the present invention.
Figure 2:
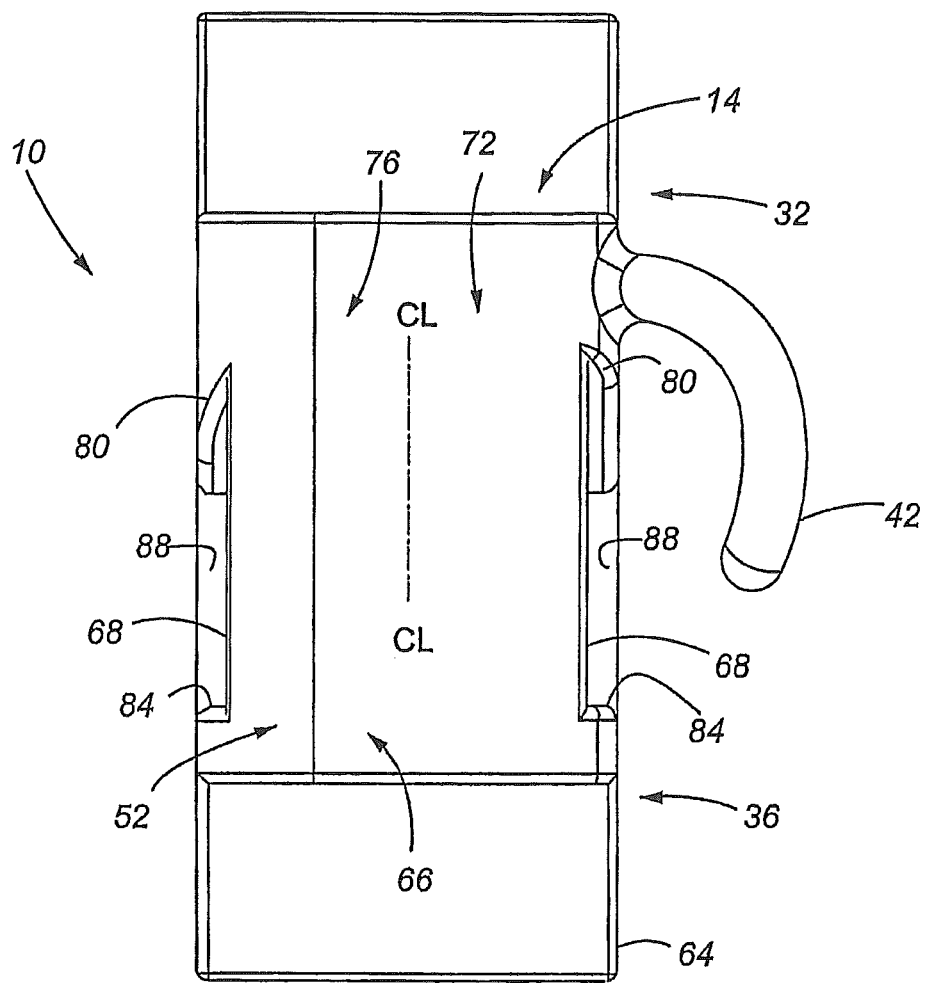
FIG. 2 is a plan view of the device shown in FIG. 1A.
Figure 3:
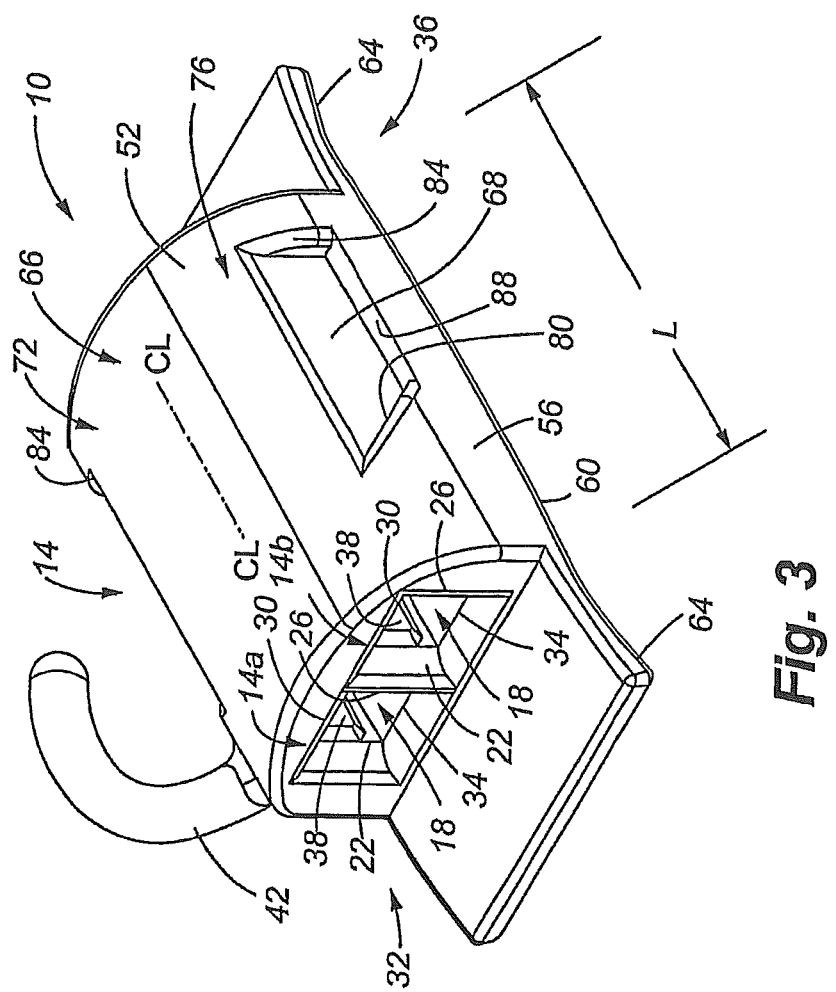
FIG. 3 is a perspective view of the device shown in FIG. 1A.
Figure 4:
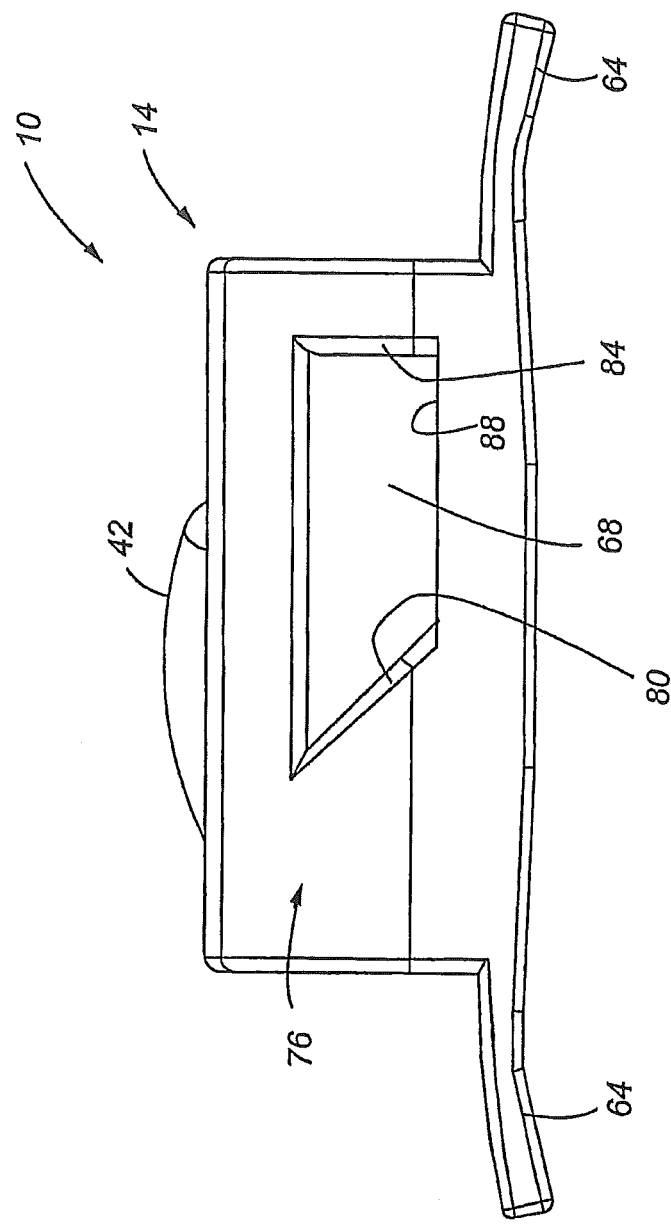
FIG. 4 is a side elevation view of the device shown in FIG. 1A.
Figure 12B:
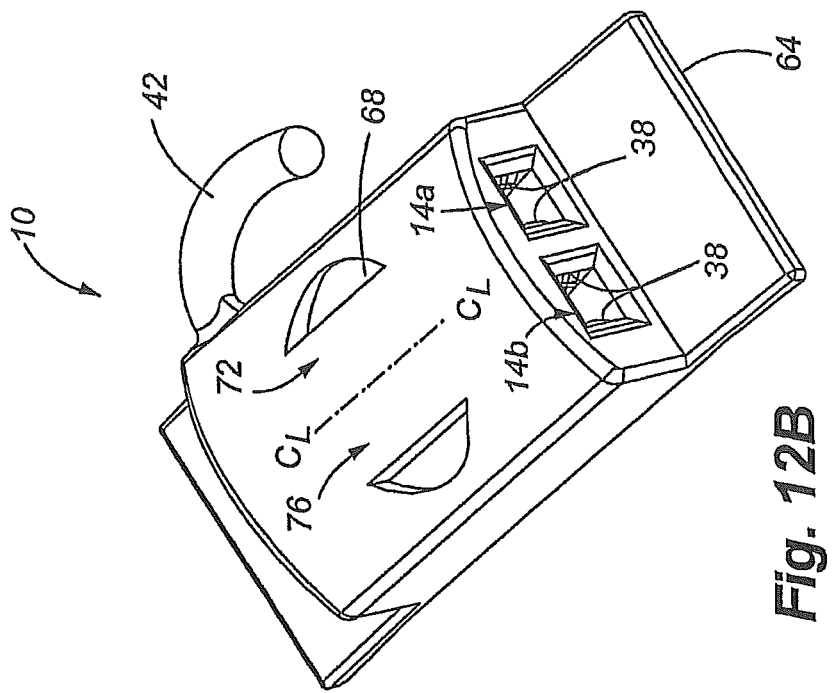
FIG. 12B is a perspective view of the device shown in FIG. 12A.
Figure 12A:
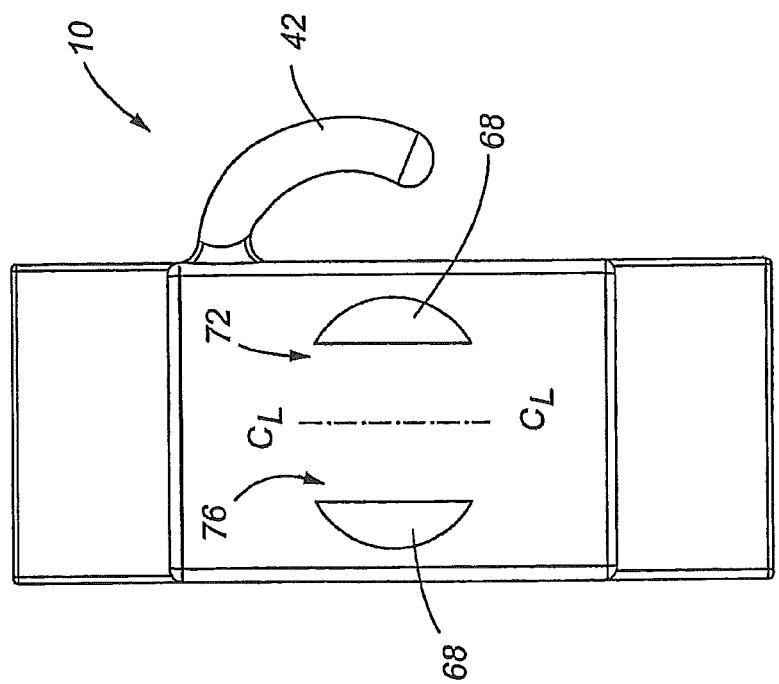
FIG. 12A is a plan view of an orthodontic appliance in accordance with embodiments of the present invention.
Figures 13A, 13B:
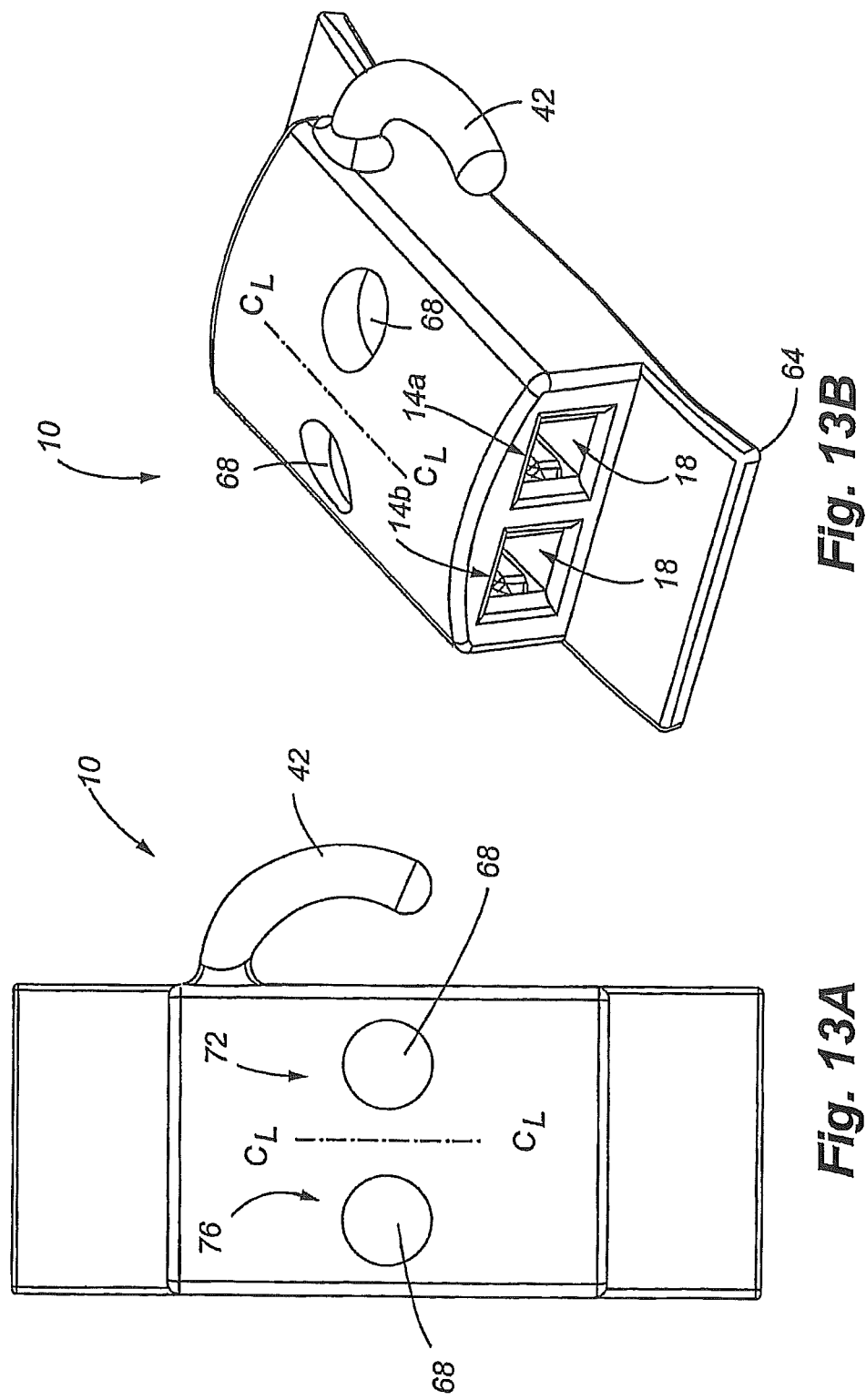
FIG. 13A is a plan view of an orthodontic appliance in accordance with embodiments of the present invention.
FIG. 13B is a perspective view of the device shown in FIG. 13A.

For the buccal tube 10 shown in FIG. 1A, the buccal tube 10 features two archwire slots (or appliance slots/tubes), namely, archwire/appliance slot/tube 14a and archwire/appliance slot/tube 14b. Accordingly, the buccal tube 10 of FIG. 1A may be characterized as a first molar, double non-convertible buccal tube with a hook. Although a non-convertible buccal tube is shown in FIG. 1A, it is to be understood that aspects of the present invention are also applicable to convertible buccal tube brackets, such as those disclosed in U.S. Pat. No. 6,428,314 entitled "Convertible Buccal Tube" and U.S. Provisional Patent Application Ser. No. 60/795,611 entitled "Orthodontic Bracket With Convertible Buccal Tube"; the contents of the foregoing patent and patent application are incorporated herein by this reference in their entireties. Furthermore, the present invention is also applicable to buccal tubes having one, two, three or more archwire/appliance slots/tubes 14. For example, in accordance with embodiments of the present invention, FIG. 1B depicts a first molar, single non-convertible buccal tube 10 with a hook.

The use of multiple archwire/appliance slots/tubes in the same buccal tube allows the treating orthodontist to apply a single buccal tube to the patient's tooth, and utilize either one or more than one of the archwire/appliance slots/tubes. For the buccal tube 10 shown in FIG. 1A, the orthodontist could use one or both of the archwire/appliance slots/tubes 14a, 14b during the various phases of treatment. Among its uses, the different archwire/appliance slot/tube locations on the buccal tube allow for the force/torque to be applied to the tooth along different points or lines of influence for each archwire/appliance slot/tube 14a, 14b.

For the buccal tube 10 shown in FIG. 1A, each archwire/appliance slot/tube 14a, 14b extends in a mesial-distal direction. Again, the present invention also applies to buccal tubes having one or more than two archwire/appliance slots/tubes, and the following discussion is directed to a single archwire/appliance slot/tube 14a to discuss the features of the archwire/appliance slot/tube. However, the discussion applies equally to other archwire/appliance slots/tubes that may be associated with the buccal tube, such as archwire/appliance slot/tube 14b shown in buccal tube 10 of FIG. 1A.

In accordance with embodiments of the present invention, the archwire/appliance slot/tube 14a includes an interior opening 18 bordered by four interior sides, namely, a gingival side 22, an occlusal side 26, a buccal side 30, and a lingual side 34. Of course, depending upon the orientation of the buccal tube 10 in the patient's mouth, the gingival side 22 and occlusal side 26 may be reversed.

In accordance with embodiments of the present invention, at least one of the interior sides 22, 26, 30 and 34, and more preferably, more than one of the interior sides 22, 26, 30 and 34 of the archwire/appliance slot/tube 14a include a feature to reduce the amount of friction developed between an archwire and the archwire/appliance slot/tube 14a. More particularly, for the buccal tube 10 shown in FIG. 1A, the archwire/appliance slot/tube 14a includes a projection 38 residing on at least one of the interior sides 22, 26, and 34. For the buccal tube 10 shown in FIG. 1A, both of the gingival side 22 and the occlusal side 26 include at least one projection 38 to reduce the amount of surface area contact between the side of the archwire and the gingival side 22 and the occlusal side 26 of the archwire/appliance slot/tube 14a. FIGS. 5A and 5B illustrate a version of a buccal tube 10, and FIGS. 5C and 5D illustrate another version of a buccal tube 10. Buccal tubes 10 of FIGS. 5A-5B and 5C-5D, have twin archwire/appliance slots/tubes 14a and 14b, wherein the gingival side 22, occlusal side 26, and buccal side 30 of the interior of the archwire/appliance slots/tubes 14a and 14b each include projections 38. By providing the projections 38 along one or more of the interior sides 22, 26, 30 and 34, the binding friction between the archwire and the buccal tube buccal tube 10 is reduced, thereby providing improved performance of the buccal tube 10 to adjust the patient's tooth. It is noted that at least some embodiments of the present invention do not include a projection along the lingual side 34 of the archwire/appliance slots/tubes 14a and 14b. As discussed in more detail below, the friction reducing features preferably comprises at least one of: (a) a plurality of longitudinally aligned projections residing along a longitudinal length of one or more of the gingival side 22, occlusal side 26, buccal side 30, and lingual side 34; and (b) a longitudinally extending projection residing along a longitudinal length of one or more of the gingival side 22, occlusal side 26, buccal side 30, and lingual side 34. In accordance with embodiments of the present invention, one or more projections are located along at least two of the gingival side 22, occlusal side 26, and buccal side 30 the interior of the archwire slot 14.

Referring now to FIG. 5E, an embodiment one of a gingival side 22, an occlusal side 26, a buccal side 30, or a lingual side 34 of an archwire/appliance slots/tube 14 is shown, wherein other portions of the buccal tube 10, including the remaining sides, are not depicted for clarity. The mesial end 32 of the interior side 22, 26, 30, 34 includes projection 38a that comprises a rounded feature. The distal end 36 of the interior side 22, 26, 30, and 34 also includes a projection 38b. For the embodiment shown in FIG. 5E, the projection 38a is not continuous with projection 38b along interior side 22, 26, 30, 34. That is, the projections 38a and 38b are spaced apart along a longitudinal length of the interior side 22, 26, 30, 34. Accordingly, projection 38a is longitudinally spaced apart but longitudinally aligned with projection 38b. An archwire A is shown extending in a mesial-distal direction that substantially corresponds to the mesial-distal orientation of the interior side 22, 26, 30, 34. The projections 38a and 38b cause a limited amount of the archwire A to contact a surface of the interior side 22, 26, 30, 34. For the example shown in FIG. 5E, the archwire A has a substantially rectangular or square shape in cross section (although the buccal tubes 10 described herein will receive archwires of different cross sectional shapes, such as round), and a side 40 of the archwire A contacts the projections 38a and 38b along a crown or ridge line 44 of the projections 38a and 38b. As a result, the archwire does not contact the majority of the length of the interior side 22, 26, 30, 34 because the projections 38a and 38b cause the archwire to be spaced apart from the surface 39 of interior side 22, 26, 30, 34, such as by a distance D.

Referring now to FIG. 5F, there is shown an embodiment of a projection 38 that extends in a longitudinal direction along the interior side 22, 26, 30, 34. Again, other portions of the buccal tube 10, including the remaining sides, are not depicted for clarity. The projection 38 of FIG. 5F substantially comprises a single and continuous curved surface 48 that extends in a mesial-distal orientation. For the example shown in FIG. 5F, again, the archwire A has a substantially rectangular or square shape in cross section, and a side 40 of the archwire A contacts the projection 38 along the longitudinal length of the projection 38. Given that the projection 38 has a curved surface 48 that is exposed to the side 40 of the archwire A, a limited surface area of the archwire/appliance slots/tube 14 contacts the archwire A, thereby reducing binding friction between the archwire A and the archwire/appliance slots/tube 14.

Referring still to FIGS. 5E and 5F, when multiple interior sides 22, 26, 30, 34 of the archwire/appliance slots/tube 14 include the friction reducing features of the one or more inventions described herein (such as projection 38 or projections 38a and 38b), additional reductions in binding friction are provided. However, the projections 38 (or projections 38a and 38b) still provide control of the archwire A along the longitudinal length of the archwire/appliance slots/tube 14 because the projections 38 (or projections 38a and 38b) engage the archwire A at more than one point along the archwire A.

Referring still to FIGS. 5E and 5F, the drawings further illustrate tapered ends 54 at the mesial end 32 and distal end 36 of the interior sides 22, 26, 30 and 34. The tapered ends 54 further reduce friction between the archwire/appliance slots/tube 14 and the archwire A.

Although discussed in terms of a projection 38, the surface area reducing feature may alternately comprise other ways of reducing friction within the archwire/appliance slot/tube 14, including a recess or multiple recesses along one or more of the interior sides 22, 26, 30 and 34. In general, the reduced friction portion of the interior opening 18 limits the amount of surface area that an archwire of any shape will be touching in the length of the opening 18 of the archwire/appliance slot/tube 14a. By way of example and not limitation, and as shown in FIGS. 5A-8D, the projections may take on a variety of shapes. The binding friction is thus reduced, including at the corners 16 of the archwire/appliance slot/tube 14a.

Embodiments of the reduced friction archwire/appliance slot/tube 14a have application for use in a molar (buccal) orthodontic tube, as well as any buccal tube including molar tubes, regular tubes and brackets of any kind that include a slot/tube structure. For buccal tube 10 shown in FIG. 1A, the buccal tube 10 further comprises a hook 42 for facilitating attachment of another device to the buccal tube 10. However, it is to be understood that the hook 42 is optional.

In accordance with at least some embodiments of the present invention, the frictional reducing features along one or more of the interior sides 22, 26, 30 and 34 are positioned to provide contact between the one or more of the interior sides 22, 26, 30 and 34 and the archwire at or near at least the mesial and distal ends the archwire/appliance slot/tube 14a, such as shown for one of the interior sides 22, 26, 30, and 34 depicted in FIG. 5E. Alternatively, the friction reducing features extend substantially the entire interior length of the interior sides having the feature, such as shown for one of the interior sides 22, 26, 30, and 34 depicted in FIG. 5F. In this way, the clinical control of the buccal tube 10 is preserved because the archwire/appliance slot/tube 14a is able to influence the archwire along substantially its entire mesial-distal length while still reducing the binding friction associated with contacting the archwire/appliance slot/tube 14a contacting the archwire.

In a separate aspect of one or more inventions described herein, at least some embodiments of buccal tube 10 include a rounded exterior occlusal surface 52. The rounded occlusal surface 52 provides for improved patient comfort, and thus, better patient satisfaction and cooperation with the treating orthodontist. In accordance with embodiments of the present invention, and as seen in the embodiments illustrated in FIGS. 1A-4 and 8A-8D, the buccal tube 10 incorporates a substantially planar surface portion 56 extending from an occlusal-base edge 60 near the base 64, that leads continuously into a relatively large radius rounded exterior occlusal surface 52 to give the exaggerated rounded surface on the occlusal side of the buccal tube 10. The buccal tube 10 may include a substantially planar surface portion 58 extending from a gingival-base edge 62 near the base 64. Accordingly, in accordance with at least one embodiment of the present invention, the archwire/appliance slot/tube 14 is not completely dome-shaped on the top or buccal side because of (1) the presence of the flat or planar surface portion 56, as well as (2) the presence of planar surface portion 58. The rounded exterior occlusal surface 52 preferably extends substantially the entire mesial/distal longitudinal length L of the archwire/appliance slot/tube 14, and can be a variety of radius sizes depending on the overall size of the archwire/appliance slot/tube 14.

Referring now to FIGS. 2, 3, 4, 7D, 8B, 8D, and 9A-15B, and in accordance with at least one embodiment of one or more inventions described herein, the buccal tube 10 includes a way for receiving an installation tool. More particularly, the exterior surface 66 may comprise at least one, and more preferably, a pair of tool receiving surfaces or receptacles for communication with an installation tool during placement of the buccal tube 10 on the patient's tooth. The inset receptacles 68 are preferably located on opposite sides of a longitudinally oriented centerline CL-CL of the buccal tube 10 (or on opposite sides of a longitudinally oriented centerline of the archwire/appliance slot/tube 14 if a single slot is present, such as shown in FIG. 1B), such as being inset within the exterior surface 66 of the archwire/appliance slots/tubes 14a, 14b. More particularly, one receptacle 68 is preferably located on the gingival side 72 of the centerline CL-CL, and the other receptacle 68 is preferably located on the occlusal side 76 of the centerline CL-CL of the buccal tube 10. In accordance with embodiments of the present invention, the receptacles 68 include a substantially planar area on the gingival and occlusal sides 72 and 76, respectively, of the centerline CL-CL of the exterior surface 66 of buccal tube 10.

The receptacles 68 may be configured for use with a direct bond tweezers, such as RMO i-1102/RMO T01102 tweezers. For the buccal tube 10 shown in FIGS. 2-4, the receptacles 68 include a sloped mesial edge 80 trending in a mesial to distal direction from the buccal to the lingual side of the receptacle 68. In contrast, the distal end 84 of the receptacles 68 is typically not sloped in a mesial to distal direction. The receptacles 68 further include a lingual ledge 88. By way of example and not limitation, FIGS. 2, 3, 4, 7D, 8B, 8D, and 9A-15B include a variety of shapes that may be used to form the receptacles 68.

In accordance with embodiments of the present invention, the appliance may comprise at least one receptacle in the exterior surface, the receptacle comprising a tool receiving surface adapted for cooperating with a placement tool, the tool receiving surface comprising a single projection and a single indentation. In accordance with embodiments of the present invention, the appliance may comprise at least a second receptacle in the exterior surface, the second receptacle comprising a tool receiving surface adapted for cooperating with the placement tool, the tool receiving surface comprising a single projection and a single cavity or indentation. In accordance with embodiments of the present invention, the appliance may comprise at least one receptacle in the exterior surface, the receptacle for receiving a tool that applies a force directed outward from a center of the receptacle.

In use, the shape of the receptacle 68 cooperates with the angle of the installation tool or tweezers, such that the installer of the buccal tube 10 is able to manipulate the buccal tube 10 to go straight into the patient's mouth, thus relieving the installer of relatively large movements of the cheek.

Figure 16:
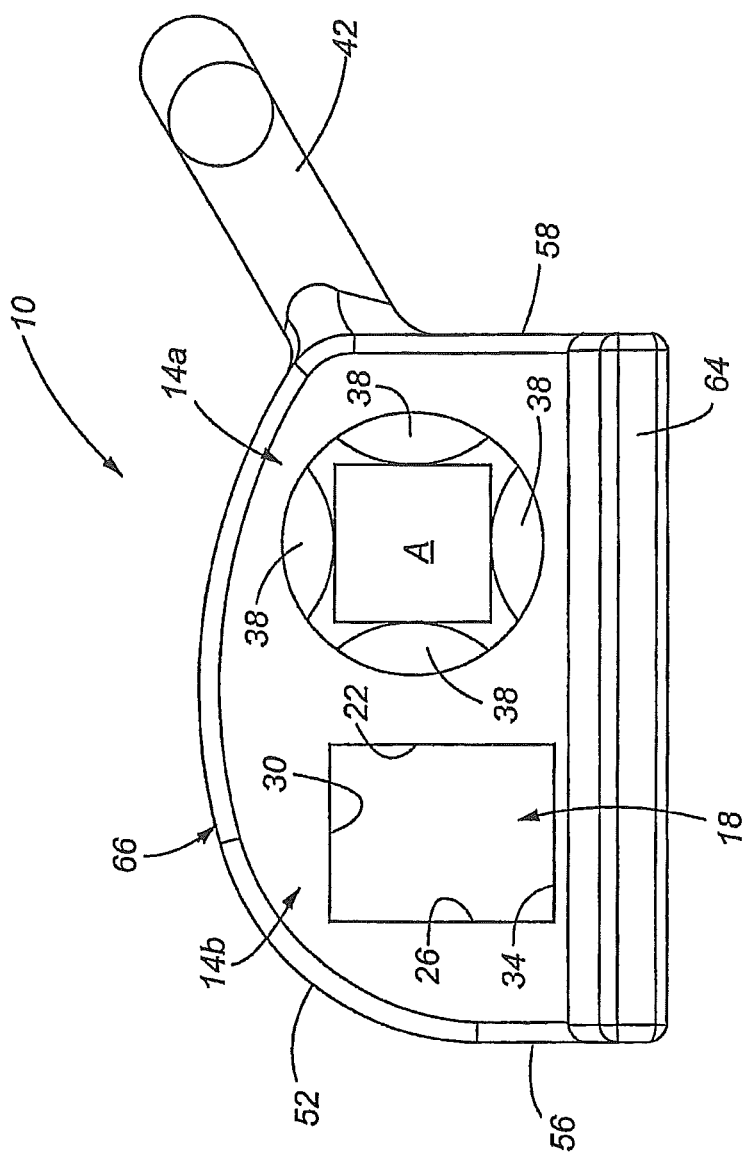
FIG. 16 is a side elevation view of a distal end of an orthodontic appliance in accordance with embodiments of the present invention.

Referring now to FIG. 16, and in accordance with at least one embodiment of one or more inventions described herein, a buccal tube 10 is shown having a pair of archwire/appliance slots/tubes 14a and 14b. The first archwire/appliance slot/tube 14a is substantially circular in cross section and includes a plurality of projections 38. The projections limit the surface area contact between the exterior sides of the archwire A and the interior of the archwire/appliance slot/tube 14a.

In a separate aspect of one or more embodiments of the one or more inventions described herein, a buccal tube 10 is provided that has at least one archwire/appliance slot/tube that includes projections for reducing frictional interaction with an archwire, and at least one archwire/appliance slot/tube that does not include projections, such as for reducing frictional interaction with an archwire. Referring again to FIG. 16, the first archwire/appliance slot/tube 14a includes at least one projection 38, and a second archwire/appliance slot/tube 14b is depicted that does not include a projection 38.

In accordance with embodiments of the present invention, a method of adjusting the position of a tooth is provide, the method including attaching a buccal tube to a tooth and inserting an archwire through an archwire slot in the buccal tube. The method further includes limiting surface contact of the archwire along a portion of the longitudinal length of the archwire slot by contacting an exterior surface of the archwire with friction reducing features located within the archwire slot. More particularly, the method includes contacting the exterior surface of the archwire with one or more of the interior sides of the archwire slot, wherein the interior sides include a gingival side, an occlusal side, a buccal side, and a lingual side. The friction reducing features preferably comprises at least one of: (a) a plurality of projections residing along a longitudinal length of one or more of the gingival side, occlusal side, buccal side, and lingual side; and (b) a longitudinally extending projection residing along a longitudinal length of one or more of the gingival side, occlusal side, buccal side, and lingual side. In accordance with embodiments of the present invention, one or more projections are located along a plurality of the gingival side, buccal side, and lingual side of the interior of the archwire slot.

It should be understood that the scope of the present invention includes the use of a plurality of passageways, including at least one passageway, and more preferably, at least two passageways, and potentially three or more passageways in any particular device. Such passageways can be configured in various symmetrical shapes and configurations to include squares, rectangles, triangles, polygons, octagons, flat and curved sided configurations, etc. In a preferred embodiment, the geometrical configuration of a passageway mirrors the general exterior shape of an archwire used with such appliance. It is also within the scope of the present invention that frangible covers abutting or extending over an archwire placed within the orthodontic device of the present invention, be removable and/or adjusted in ways desired by an orthodontist. Thus, for example, materials rounding receptacle 68 can be constructed so as to be frangible and thus removable at some point in time after desired placement of a device and/or for orientation thereof. The number of receptacles 68 can include, for example, at least one receptacle suitable for manipulation by an orthodontist, but may also include one or more, two or more, or three or more such receptacles, which can, in certain embodiments, be adapted to correlate with the prongs of a receptacle engaging device or insertion tool. One of skill in the art will also appreciate the scope of the present invention includes the use of different geometrically configured passageways, such that a square archwire can be used in one passageway, whereas a round archwire can be used in an adjacent passageway, etc., with the passageways having a similar exterior configuration as the archwire utilized in such applications. Alternatively, the passageway or archwire slot may have a different geometric shape than that of the archwire used.

In summation, a buccal tube is provided that includes a number of novel features, including a friction reducing profile within the buccal tube opening, modified exterior shaping to facilitate improved comfort, and a plurality of positioning notches, buccal recesses, gripping portions or placement notches for receiving an installation tool. For the above-described buccal tube 10, placement of the archwire/appliance slot/tube 14 on a band can cover any angle, mesial/distal locations, gingival/occlusal locations, and any direct bond applications.

One or more inventions may be described herein, and embodiments shown and/or described may comprise one or more of the inventions.

A number of variations and modifications of the invention can be used. It would be possible to provide for some features of the invention without providing others. For example, in one alternative embodiment, a low friction archwire/appliance slot/tube may be used without a rounded exterior occlusal surface, and without the installation tool receiving receptacles. In another alternative embodiment, the receptacles may be used on a buccal tube having gingival and occlusal surfaces, but without a low friction archwire/appliance slot/tube for receiving an archwire, and without a rounded exterior occlusal surface.

The present invention, in various embodiments, includes components, methods, processes, systems and/or apparatus substantially as depicted and described herein, including various embodiments, subcombinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, e.g., for improving performance, achieving ease and/or reducing cost of implementation.

The foregoing discussion of the invention has been presented for purposes of illustration and description. The foregoing is not intended to limit the invention to the form or forms disclosed herein. In the foregoing Detailed Description Of The Invention for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description Of The Invention, with each claim standing on its own as a separate preferred embodiment of the invention.

Moreover, although the description of the invention has included description of one or more embodiments and certain variations and modifications, other variations and modifications are within the scope of the invention, e.g., as may be within the skill and knowledge of those in the art, after understanding the present disclosure. It is intended to obtain rights that include alternative embodiments to the extent permitted, including alternate, interchangeable and/or equivalent structures, functions, ranges or steps to those claimed.

What is claimed is:

1. An orthodontic appliance for cooperating with an archwire, the appliance comprising:
    a base having a substantially uniform thickness extending the length of the appliance;
    at least one archwire tube connected to said base, the at least one archwire tube comprising: (i) a first aperature, (ii) a second aperature, and (iii) a passageway having a length between said first and second aperatures, wherein the passageway is adapted for receiving the archwire;
    wherein the passageway comprises interior sides; wherein the interior sides comprise a gingival side, an occlusal side, a lingual side and a buccal side;
    wherein the buccal side comprises a friction reducing feature and wherein at least one of the group consisting of the gingival side, the occlusal side and the lingual side comprises a friction reducing feature; wherein a first of the friction reducing features comprises a projection extending substantially the length of said passageway and extending into said passageway;

wherein the first of the friction reducing features reduces contact of the archwire with a first predetermined portion of the passageway;

wherein a second of the friction reducing features comprises a plurality of separate projections residing along the length of said passageway, projecting into said passageway and spaced apart from each other along the length of said passageway;

wherein the second of the friction reducing features reduces contact of the archwire with a second predetermined portion of the passageway; and said passageway having at least one tapered end at one of a mesial end and a distal end of said passageway.

2. The appliance as claimed in claim 1, wherein said passageway has a tapered mesial end and a tapered distal end.

3. The appliance as claimed in claim 1, further comprising at least one receptacle having a tool receiving surface inset from an exterior surface of the appliance, said at least one receptacle located on one of an occlusal side of a longitudinally-oriented centerline of said appliance, and a gingival side of the longitudinally oriented centerline.

4. The appliance as claimed in claim 1, further comprising a hook for attaching a device to the appliance.

5. The appliance as claimed in claim 1, further comprising at least one receptacle in an exterior surface of the appliance, the at least one receptacle comprising a tool receiving surface adapted for cooperating with a placement tool for positioning the appliance.

6. The appliance as claimed in claim 1, further comprising at least one receptacle in said exterior surface, the at least one receptacle for receiving a tool.

7. An orthodontic appliance for cooperating with an archwire, the appliance comprising:
a base extending the length of the appliance;
an archwire tube connected to said base;
an auxiliary tubular body being in substantially side-by-side relationship with said archwire tube;
the archwire tube comprising: (i) a first aperature, (ii) a second aperature, and (iii) a passageway having a length between said first and second aperatures, wherein the passageway is adapted for receiving the archwire;
wherein the passageway comprises interior sides; wherein the interior sides comprise a gingival side, an occlusal side, a lingual side and a buccal side;
the buccal side comprises a friction reducing feature and wherein at least one of the group consisting of the gingival side, the occlusal side and the lingual side comprises a friction reducing feature;
wherein a first of the friction reducing features comprises a projection extending substantially the length of said passageway and extending into said passageway; wherein the first of the friction reducing features reduces contact of the archwire with a first predetermined portion of the passageway;
wherein a second of the friction reducing features comprises a plurality of separate projections residing along the length of said passageway, projecting into said passageway and spaced apart from each other along the length of said passageway;
wherein the second of the friction reducing features reduces contact of the archwire with a second predetermined portion of the passageway;

wherein said auxiliary tubular body has an auxiliary tubular body passageway adapted for receiving an archwire; wherein the auxiliary tubular body passageway comprises interior sides; wherein the interior sides comprise a gingival side, an occlusal side, a lingual side and a buccal side; wherein the buccal side comprises a friction reducing feature and wherein at least one of the group consisting of the gingival side, the occlusal side and the lingual side comprises a friction reducing feature.

8. The appliance as claimed in claim 7, further comprising a hook for attaching a device to the appliance.

9. The appliance as claimed in claim 7, wherein said auxiliary tubular body passageway has at least one tapered end at one of a mesial end and a distal end of said auxiliary tubular body passageway.

10. The appliance as claimed in claim 7, wherein said auxiliary tubular body passageway has a tapered mesial end and a tapered distal end.

11. The appliance as claimed in claim 7, further comprising at least one receptacle in an exterior surface of the appliance, the at least one receptacle comprising a tool receiving surface adapted for cooperating with a placement tool for positioning the appliance.

12. An orthodontic appliance for cooperating with an archwire, the appliance comprising:
a base extending the length of the appliance;
a first archwire tube connected to said base, the first archwire tube comprising: (i) a first aperature, (ii) a second aperature, and (iii) a first passageway having a length between said first and second aperatures, wherein the passageway is adapted for receiving the archwire;
wherein the first passageway comprises interior sides; wherein the interior sides comprise a gingival side, an occlusal side, a lingual side and a buccal side;
wherein the buccal side comprises a friction reducing feature and wherein at least one of the group consisting of the gingival side, the occlusal side and the lingual side comprises a friction reducing feature; wherein a first of the friction reducing features comprises a projection extending substantially the length of said passageway and extending into said passageway;
wherein the first of the friction reducing features reduces contact of the archwire with a first predetermined portion of the first passageway;
wherein a second of the friction reducing features comprises at least two separate projections residing along the length of said first passageway, projecting into said first passageway and spaced apart from each other along the length of said first passageway; wherein the second of the friction reducing features reduces contact of the archwire with a second predetermined portion of the first passageway; wherein said first passageway has at least one tapered end at one of a mesial end and a distal end of said first passageway; and
a second archwire tube extending parallel to said first archwire tube.

13. The appliance as claimed in claim 12, wherein a topmost portion of said appliance is curved.

14. The appliance as claimed in claim 12, wherein a hook is integral with said appliance.

15. The appliance as claimed in claim 12, wherein the second archwire tube has a distal and a mesial end and has a second passageway extending between said distal end and mesial end, said second passageway having a taper at one of said distal end and said mesial end.

16. The appliance as claimed in claim 12, wherein said appliance has at least one receptacle having a tool receiving surface.

17. The appliance as claimed in claim 12, wherein said first archwire tube and said second archwire tube are in a side-by-side relationship.

18. The appliance as claimed in claim 12, wherein said first archwire tube and said second archwire tube extend the same distance above the base.

19. The appliance as claimed in claim 12, wherein said first archwire tube and said second archwire tube are integral with each other.

20. The appliance as claimed in claim 12, wherein said second passageway has a taper at both of said distal end and said mesial end.

* * * * *